(12) United States Patent
Navia et al.

(10) Patent No.: US 12,427,016 B2
(45) Date of Patent: Sep. 30, 2025

(54) APPARATUS AND METHOD FOR REPLACING A DISEASED CARDIAC VALVE

(71) Applicant: Edwards Lifesciences Corporation, Irvine, CA (US)

(72) Inventors: Jose Luis Navia, Shaker Heights, OH (US); Ji-Feng Chen, Lakewood, OH (US); Qun Zhou, Lakewood, OH (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1101 days.

(21) Appl. No.: 17/067,580

(22) Filed: Oct. 9, 2020

(65) Prior Publication Data

US 2021/0161657 A1 Jun. 3, 2021

Related U.S. Application Data

(63) Continuation of application No. 12/769,593, filed on Apr. 28, 2010, now abandoned.

(Continued)

(51) Int. Cl.
*A61F 2/24* (2006.01)

(52) U.S. Cl.
CPC .......... *A61F 2/2418* (2013.01); *A61F 2/2412* (2013.01); *A61F 2/2436* (2013.01);
(Continued)

(58) Field of Classification Search
None
See application file for complete search history.

(56) References Cited

U.S. PATENT DOCUMENTS

| | | |
|---|---|---|
| 3,409,013 A | 11/1968 | Berry |
| 3,472,230 A | 10/1969 | Fogarty |

(Continued)

FOREIGN PATENT DOCUMENTS

| | | |
|---|---|---|
| CA | 2304325 A1 | 10/2000 |
| DE | 2246526 A1 | 3/1973 |

(Continued)

OTHER PUBLICATIONS

Andersen, et al. "Transluminal implantation of artificial heart valves. Description of a new expandable aortic valve and inital results with implantation by catheter technique in closed chest pigs." European Heart Journal (1992), 13, 704-708.

(Continued)

*Primary Examiner* — Leslie A Lopez
(74) *Attorney, Agent, or Firm* — Thomas C. Richardson

(57) ABSTRACT

An apparatus is provided for replacing a native cardiac valve. The native cardiac valve has at least one leaflet and is surrounded by a native cardiac valve annulus having superior and inferior aspects. The apparatus comprises a barbell-shaped, expandable anchoring member including first, second, and main body portions extending between the end portions. The main body portion includes a channel defined by inner and outer surfaces. Each of the first and second end portions has a diameter greater than the diameter of the main body portion. The first and second end portions are sized to respectively contact the superior and inferior aspects of the native cardiac valve annulus when the expandable anchoring member is in an expanded configuration. The apparatus also includes an expandable support member operably disposed within the main body portion of the expandable anchoring member, and a prosthetic cardiac valve secured within the expandable support member.

19 Claims, 12 Drawing Sheets

Related U.S. Application Data

(60) Provisional application No. 61/173,782, filed on Apr. 29, 2009.

(52) U.S. Cl.
CPC ............ *A61F 2210/0004* (2013.01); *A61F 2210/0014* (2013.01); *A61F 2220/0008* (2013.01); *A61F 2220/005* (2013.01); *A61F 2220/0066* (2013.01); *A61F 2220/0075* (2013.01); *A61F 2230/0054* (2013.01); *A61F 2230/0069* (2013.01); *A61F 2230/0078* (2013.01); *A61F 2250/006* (2013.01); *A61F 2250/0098* (2013.01); *A61F 2310/00023* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,011,947 A | 3/1977 | Sawyer |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goecoechea et al. |
| 6,306,141 B1 | 10/2001 | Jervis |
| 6,312,465 B1 | 11/2001 | Griffin et al. |
| 6,338,740 B1 * | 1/2002 | Carpentier ............ A61F 2/2427 623/2.12 |
| 6,350,277 B1 | 2/2002 | Kocur |
| 6,358,277 B1 | 3/2002 | Duran |
| 6,379,372 B1 | 4/2002 | Dehdashtian et al. |

(56) References Cited

U.S. PATENT DOCUMENTS

| | | | |
|---|---|---|---|
| 6,425,916 B1 * | 7/2002 | Garrison | A61F 2/2436 |
| | | | 623/2.11 |
| 6,440,164 B1 | 8/2002 | Matteo et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,800 B1 | 3/2003 | McGuckin, Jr. et al. | |
| 6,527,979 B2 | 3/2003 | Constantz | |
| 6,534,004 B2 * | 3/2003 | Chen | A61L 2/08 |
| | | | 422/1 |
| 6,540,782 B1 | 4/2003 | Snyders | |
| 6,569,196 B1 | 5/2003 | Vesely | |
| 6,575,959 B1 | 6/2003 | Sarge et al. | |
| 6,582,462 B1 | 6/2003 | Andersen et al. | |
| 6,605,112 B1 | 8/2003 | Moll et al. | |
| 6,610,088 B1 | 8/2003 | Gabbay | |
| 6,629,534 B1 | 10/2003 | Goar et al. | |
| 6,676,698 B2 | 1/2004 | McGuckin, Jr. et al. | |
| 6,695,878 B2 | 2/2004 | McGuckin, Jr. et al. | |
| 6,712,836 B1 | 3/2004 | Berg et al. | |
| 6,716,207 B2 | 4/2004 | Farnholtz | |
| 6,729,356 B1 | 5/2004 | Baker et al. | |
| 6,730,118 B2 | 5/2004 | Spenser et al. | |
| 6,733,525 B2 | 5/2004 | Yang et al. | |
| 6,746,422 B1 | 6/2004 | Noriega et al. | |
| 6,749,560 B1 | 6/2004 | Konstorum et al. | |
| 6,767,362 B2 | 7/2004 | Schreck | |
| 6,780,200 B2 | 8/2004 | Jansen | |
| 6,790,229 B1 | 9/2004 | Berreklouw | |
| 6,790,230 B2 | 9/2004 | Beyersdorf et al. | |
| 6,821,297 B2 | 11/2004 | Snyders | |
| 6,830,584 B1 | 12/2004 | Seguin | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,974,476 B2 | 12/2005 | McGuckin, Jr. et al. | |
| 7,018,406 B2 | 3/2006 | Seguin et al. | |
| 7,186,265 B2 | 3/2007 | Sharkawy et al. | |
| 7,192,440 B2 | 3/2007 | Andreas et al. | |
| 7,198,646 B2 | 4/2007 | Figulla et al. | |
| 7,201,772 B2 | 4/2007 | Schwammenthal et al. | |
| 7,276,078 B2 | 10/2007 | Spenser et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,381,210 B2 | 6/2008 | Zarbatany et al. | |
| 7,381,219 B2 | 6/2008 | Salahieh et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| 7,445,631 B2 | 11/2008 | Salahieh et al. | |
| 7,462,191 B2 | 12/2008 | Spenser et al. | |
| 7,510,575 B2 | 3/2009 | Spenser et al. | |
| 7,524,330 B2 | 4/2009 | Berreklouw | |
| 7,530,253 B2 | 5/2009 | Spenser et al. | |
| 7,530,995 B2 | 5/2009 | Quijano et al. | |
| 7,553,324 B2 | 6/2009 | Andreas et al. | |
| 7,579,381 B2 | 8/2009 | Dove | |
| 7,585,321 B2 | 9/2009 | Cribier | |
| 7,618,446 B2 | 11/2009 | Andersen et al. | |
| 7,621,948 B2 | 11/2009 | Herrmann et al. | |
| 7,704,222 B2 | 4/2010 | Wilk et al. | |
| 7,736,327 B2 | 6/2010 | Wilk et al. | |
| 7,748,389 B2 | 7/2010 | Salahieh et al. | |
| 7,753,949 B2 | 7/2010 | Lamphere et al. | |
| 7,806,919 B2 | 10/2010 | Bloom et al. | |
| 7,824,443 B2 | 11/2010 | Salahieh et al. | |
| 7,837,727 B2 | 11/2010 | Goetz et al. | |
| 7,892,281 B2 | 2/2011 | Seguin et al. | |
| 7,914,569 B2 | 3/2011 | Nguyen et al. | |
| 7,914,575 B2 | 3/2011 | Guyenot et al. | |
| 7,959,672 B2 | 6/2011 | Salahieh et al. | |
| 7,972,378 B2 | 7/2011 | Tabor et al. | |
| 7,981,151 B2 | 7/2011 | Rowe | |
| 7,993,392 B2 | 8/2011 | Righini et al. | |
| 7,993,394 B2 | 8/2011 | Hariton et al. | |
| 8,007,992 B2 | 8/2011 | Tian et al. | |
| 8,016,877 B2 | 9/2011 | Seguin et al. | |
| 8,029,556 B2 | 10/2011 | Rowe | |
| 8,052,750 B2 | 11/2011 | Tuval et al. | |
| 8,070,800 B2 | 12/2011 | Lock et al. | |
| 8,070,802 B2 | 12/2011 | Lamphere et al. | |
| 8,075,615 B2 | 12/2011 | Eberhardt et al. | |
| 8,080,054 B2 | 12/2011 | Rowe | |
| 8,092,520 B2 | 1/2012 | Quadri | |
| 8,092,521 B2 | 1/2012 | Figulla et al. | |
| 8,109,996 B2 | 2/2012 | Stacchino et al. | |
| 8,118,866 B2 | 2/2012 | Herrmann et al. | |
| 8,136,218 B2 | 3/2012 | Millwee et al. | |
| 8,137,398 B2 | 3/2012 | Tuval et al. | |
| 8,157,852 B2 | 4/2012 | Bloom et al. | |
| 8,167,932 B2 | 5/2012 | Bourang et al. | |
| 8,167,934 B2 | 5/2012 | Styrc et al. | |
| 8,182,530 B2 | 5/2012 | Huber | |
| 8,206,437 B2 | 6/2012 | Bonhoeffer et al. | |
| 8,216,174 B2 | 7/2012 | Wilk et al. | |
| 8,216,301 B2 | 7/2012 | Bonhoeffer et al. | |
| 8,219,229 B2 | 7/2012 | Cao et al. | |
| 8,220,121 B2 | 7/2012 | Hendriksen et al. | |
| 8,236,045 B2 | 8/2012 | Benichou et al. | |
| 8,246,675 B2 | 8/2012 | Zegdi | |
| 8,246,678 B2 | 8/2012 | Salahieh et al. | |
| 8,252,051 B2 | 8/2012 | Chau et al. | |
| 8,252,052 B2 | 8/2012 | Salahieh et al. | |
| 8,287,584 B2 | 10/2012 | Salahieh et al. | |
| 8,313,525 B2 | 11/2012 | Tuval et al. | |
| 8,317,858 B2 | 11/2012 | Straubinger et al. | |
| 8,323,335 B2 | 12/2012 | Rowe et al. | |
| 8,337,541 B2 | 12/2012 | Quadri et al. | |
| 8,353,953 B2 | 1/2013 | Giannetti et al. | |
| 8,398,704 B2 | 3/2013 | Straubinger et al. | |
| 8,403,983 B2 | 3/2013 | Quadri et al. | |
| 8,414,644 B2 | 4/2013 | Quadri et al. | |
| 8,414,645 B2 | 4/2013 | Dwork et al. | |
| 8,416,643 B2 | 4/2013 | Magee | |
| 8,444,689 B2 | 5/2013 | Zhang | |
| 8,449,599 B2 | 5/2013 | Chau et al. | |
| 8,454,685 B2 | 6/2013 | Hariton et al. | |
| 8,460,368 B2 | 6/2013 | Taylor et al. | |
| 8,460,370 B2 | 6/2013 | Zakay | |
| 8,470,023 B2 | 6/2013 | Eidenschink et al. | |
| 8,470,028 B2 | 6/2013 | Thornton et al. | |
| 8,475,521 B2 | 7/2013 | Suri et al. | |
| 8,475,523 B2 | 7/2013 | Duffy | |
| 8,479,380 B2 | 7/2013 | Malewicz et al. | |
| 8,491,650 B2 | 7/2013 | Wiemeyer et al. | |
| 8,500,733 B2 | 8/2013 | Watson | |
| 8,500,798 B2 | 8/2013 | Rowe et al. | |
| 8,511,244 B2 | 8/2013 | Holecek et al. | |
| 8,512,401 B2 | 8/2013 | Murray et al. | |
| 8,518,096 B2 | 8/2013 | Nelson | |
| 8,518,106 B2 | 8/2013 | Duffy et al. | |
| 8,562,663 B2 | 10/2013 | Mearns et al. | |
| 8,579,963 B2 | 11/2013 | Tabor | |
| 8,579,964 B2 | 11/2013 | Lane et al. | |
| 8,591,570 B2 | 11/2013 | Revuelta et al. | |
| 8,617,236 B2 | 12/2013 | Paul et al. | |
| 8,640,521 B2 | 2/2014 | Righini et al. | |
| 8,647,381 B2 | 2/2014 | Essinger et al. | |
| 8,652,145 B2 | 2/2014 | Maimon et al. | |
| 8,652,201 B2 | 2/2014 | Oberti et al. | |
| 8,652,202 B2 | 2/2014 | Alon et al. | |
| 8,652,203 B2 | 2/2014 | Quadri et al. | |
| 8,668,733 B2 | 3/2014 | Haug et al. | |
| 8,679,174 B2 | 3/2014 | Ottma et al. | |
| 8,679,404 B2 | 3/2014 | Liburd et al. | |
| 8,685,086 B2 | 4/2014 | Navia et al. | |
| 8,721,708 B2 | 5/2014 | Seguin et al. | |
| 8,721,714 B2 | 5/2014 | Kelley | |
| 8,728,154 B2 | 5/2014 | Alkhatib | |
| 8,728,155 B2 | 5/2014 | Montorfano et al. | |

(56) References Cited

U.S. PATENT DOCUMENTS

| | | |
|---|---|---|
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,095,434 B2 | 8/2015 | Rowe |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,295,551 B2 | 3/2016 | Straubinger et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |
| 10,758,344 B2 | 9/2020 | Hariton et al. |
| 11,406,499 B2 | 8/2022 | Zhang et al. |
| 11,452,598 B2 | 9/2022 | Essinger et al. |
| 11,672,658 B2 | 6/2023 | Hariton et al. |
| 11,701,225 B2 | 7/2023 | Hammer et al. |
| 11,903,829 B1 | 2/2024 | Ma et al. |
| 2001/0021872 A1 | 9/2001 | Bailey et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0107565 A1 | 8/2002 | Greenhalgh |
| 2002/0123802 A1 | 9/2002 | Snyders |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0105517 A1 | 6/2003 | White et al. |
| 2003/0114913 A1 | 6/2003 | Spenser et al. |
| 2003/0118560 A1* | 6/2003 | Kelly .................... A61L 27/507 |
| | | 424/424 |
| 2003/0120333 A1 | 6/2003 | Ouriel et al. |
| 2003/0130729 A1 | 7/2003 | Paniagua et al. |
| 2003/0149477 A1* | 8/2003 | Gabbay ................ A61F 2/2436 |
| | | 623/2.14 |
| 2003/0149478 A1 | 8/2003 | Figulla et al. |
| 2003/0158597 A1 | 8/2003 | Quiachon et al. |
| 2003/0176914 A1 | 9/2003 | Rabkin et al. |
| 2003/0199971 A1 | 10/2003 | Tower et al. |
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0093075 A1 | 5/2004 | Kuehne |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0159811 A1 | 7/2005 | Lane |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0052867 A1* | 3/2006 | Revuelta .............. A61F 2/2409 |
| | | 623/2.38 |
| 2006/0058872 A1 | 3/2006 | Salahieh et al. |
| 2006/0095115 A1 | 5/2006 | Bladillah et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |

(56) References Cited

U.S. PATENT DOCUMENTS

| | | |
|---|---|---|
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2006/0287719 A1* | 12/2006 | Rowe ............... A61F 2/2445 623/2.18 |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0162107 A1 | 7/2007 | Haug et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0255394 A1 | 11/2007 | Ryan |
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0161910 A1 | 7/2008 | Revuelta et al. |
| 2008/0177381 A1* | 7/2008 | Navia ............... A61F 2/2433 623/2.11 |
| 2008/0183273 A1 | 7/2008 | Mesana et al. |
| 2008/0208327 A1* | 8/2008 | Rowe ............... A61F 2/2427 604/509 |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0024818 A1 | 2/2010 | Stenzler et al. |
| 2010/0049313 A1 | 2/2010 | Alon et al. |
| 2010/0069852 A1 | 3/2010 | Kelley |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0145438 A1* | 6/2010 | Barone ............... A61F 2/2418 623/2.38 |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0029072 A1* | 2/2011 | Gabbay ............... A61F 2/2418 623/2.37 |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray, III et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0172992 A1 | 7/2013 | Gross et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |

(56) References Cited

U.S. PATENT DOCUMENTS

| | | |
|---|---|---|
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0100651 A1 | 4/2014 | Kheradvar et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214157 A1 | 7/2014 | Bortlein et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277403 A1 | 9/2014 | Peter |
| 2014/0277412 A1 | 9/2014 | Bortlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray et al. |
| 2015/0005863 A1 | 1/2015 | Para |
| 2015/0018944 A1 | 1/2015 | O'Connell et al. |
| 2015/0039083 A1 | 2/2015 | Rafiee |
| 2015/0142100 A1 | 5/2015 | Morriss et al. |
| 2015/0142103 A1 | 5/2015 | Mdlund |
| 2015/0148731 A1 | 5/2015 | Mcnamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038280 A1 | 2/2016 | Morriss et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2017/0042678 A1 | 2/2017 | Ganesan et al. |
| 2017/0079785 A1 | 3/2017 | Li |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0257902 A1 | 9/2017 | Xing et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0110622 A1 | 4/2018 | Gregg et al. |
| 2018/0116790 A1 | 5/2018 | Ratz et al. |
| 2018/0126119 A1 | 5/2018 | McNiven et al. |
| 2018/0214664 A1 | 8/2018 | Kim et al. |
| 2018/0296341 A1 | 10/2018 | Noe et al. |
| 2018/0344457 A1 | 12/2018 | Gross et al. |
| 2018/0344490 A1 | 12/2018 | Fox et al. |
| 2019/0008639 A1 | 1/2019 | Landon et al. |
| 2019/0008640 A1 | 1/2019 | Cooper et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0138572 A1 | 5/2020 | Zhao et al. |
| 2020/0323668 A1 | 10/2020 | Diedering et al. |
| 2020/0345494 A1 | 11/2020 | Srinimukesh et al. |
| 2020/0352718 A1 | 11/2020 | Rowe et al. |
| 2021/0145576 A1 | 5/2021 | Becerra et al. |
| 2021/0228354 A1 | 7/2021 | Rafiee et al. |
| 2021/0259835 A1 | 8/2021 | Tyler et al. |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |
| 2024/0091000 A1 | 3/2024 | King et al. |

FOREIGN PATENT DOCUMENTS

| | | |
|---|---|---|
| DE | 2246526 C3 | 7/1981 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 19546692 C2 | 11/2002 |
| DE | 10049812 B4 | 6/2004 |
| DE | 19857887 B4 | 5/2005 |
| DE | 10049815 B4 | 10/2005 |
| DE | 10049814 B4 | 10/2006 |
| DE | 102006052564 B3 | 12/2007 |
| EP | 0103546 A1 | 3/1984 |

(56) References Cited

FOREIGN PATENT DOCUMENTS

| | | |
|---|---|---|
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1171059 A1 | 1/2002 |
| EP | 1239901 A1 | 9/2002 |
| EP | 1259194 A1 | 11/2002 |
| EP | 1369098 A1 | 12/2003 |
| EP | 1469797 A1 | 10/2004 |
| EP | 1472996 A1 | 11/2004 |
| EP | 1088529 B1 | 6/2005 |
| EP | 1570809 A1 | 9/2005 |
| EP | 1469797 B1 | 11/2005 |
| EP | 1653888 A2 | 5/2006 |
| EP | 1849440 A1 | 10/2007 |
| EP | 1935377 A1 | 6/2008 |
| EP | 1255510 B3 | 3/2009 |
| EP | 2124826 A1 | 12/2009 |
| EP | 2168536 A1 | 3/2010 |
| EP | 2413842 A1 | 2/2012 |
| EP | 2446915 A1 | 5/2012 |
| EP | 2745805 A1 | 6/2014 |
| EP | 2749254 A1 | 7/2014 |
| EP | 2750630 A1 | 7/2014 |
| EP | 2777616 A1 | 9/2014 |
| EP | 2777617 A1 | 9/2014 |
| EP | 2918249 A2 | 9/2015 |
| EP | 2948103 A2 | 12/2015 |
| EP | 2967858 A2 | 1/2016 |
| EP | 3037064 A1 | 6/2016 |
| EP | 3046511 A2 | 7/2016 |
| EP | 3057541 A1 | 8/2016 |
| EP | 3075354 A2 | 10/2016 |
| EP | 3139864 A1 | 3/2017 |
| EP | 3142603 A1 | 3/2017 |
| EP | 3184083 A1 | 6/2017 |
| EP | 3294220 A1 | 3/2018 |
| EP | 3417813 A1 | 12/2018 |
| EP | 3570779 A1 | 11/2019 |
| EP | 2918249 B1 | 4/2020 |
| FR | 2788217 A1 | 7/2000 |
| GB | 1264471 A | 2/1972 |
| GB | 1315844 A | 5/1973 |
| GB | 2056023 A | 3/1981 |
| GB | 2056023 B | 8/1983 |
| GB | 2398245 A | 8/2004 |
| GB | 2398245 B | 3/2007 |
| SU | 1271508 A1 | 11/1986 |
| WO | 9116041 A1 | 10/1991 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9933414 A1 | 7/1999 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0061034 A1 | 10/2000 |
| WO | 0236048 A1 | 5/2002 |
| WO | WO-2002041789 A1 | 5/2002 |
| WO | 02100297 A2 | 12/2002 |
| WO | 03047468 A1 | 6/2003 |
| WO | 03092554 A1 | 11/2003 |
| WO | 2004030569 A2 | 4/2004 |
| WO | 2005011534 A1 | 2/2005 |
| WO | 2005034812 A1 | 4/2005 |
| WO | WO-2005062980 A2 | 7/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |
| WO | 2006085225 A1 | 8/2006 |
| WO | 2006108090 A2 | 10/2006 |
| WO | 2006111391 A1 | 10/2006 |
| WO | 2006138173 A2 | 12/2006 |
| WO | 2007025028 A1 | 3/2007 |
| WO | 2008005405 A2 | 1/2008 |
| WO | 2008029296 A2 | 3/2008 |
| WO | 2008035337 A2 | 3/2008 |
| WO | WO-2008029629 A1 | 3/2008 |
| WO | 2008125153 A1 | 10/2008 |
| WO | 2008147964 A1 | 12/2008 |
| WO | 2008150529 A1 | 12/2008 |
| WO | 2009024859 A2 | 2/2009 |
| WO | 2009026563 A2 | 2/2009 |
| WO | 2009042196 A2 | 4/2009 |
| WO | 2009091509 A1 | 7/2009 |
| WO | 2009094500 A1 | 7/2009 |
| WO | WO-2009116041 A2 | 9/2009 |
| WO | 2010005524 A2 | 1/2010 |
| WO | 2010008549 A1 | 1/2010 |
| WO | 2010121076 A2 | 10/2010 |
| WO | 2011002996 A2 | 1/2011 |
| WO | 2011081997 A1 | 7/2011 |
| WO | WO-2012008459 A1 | 1/2012 |
| WO | 2012032187 A1 | 3/2012 |
| WO | 2012095455 A2 | 7/2012 |
| WO | 2013005878 A1 | 1/2013 |
| WO | 2013028387 A2 | 2/2013 |
| WO | 2013106585 A1 | 7/2013 |
| WO | 2014009213 A1 | 1/2014 |
| WO | 2014018432 A2 | 1/2014 |
| WO | 2014079291 A1 | 5/2014 |
| WO | 2014145338 A1 | 9/2014 |
| WO | 2014149865 A1 | 9/2014 |
| WO | 2014163706 A1 | 10/2014 |
| WO | 2014194178 A1 | 12/2014 |
| WO | 2015004624 A1 | 1/2015 |
| WO | 2015004625 A1 | 1/2015 |
| WO | 2015057407 A1 | 4/2015 |
| WO | 2015077274 A1 | 5/2015 |
| WO | 2016002189 A1 | 1/2016 |
| WO | 2016004137 A1 | 1/2016 |
| WO | 2016016899 A1 | 2/2016 |
| WO | 2017006510 A1 | 1/2017 |
| WO | 2017035487 A1 | 3/2017 |
| WO | WO-2018000333 A1 | 1/2018 |
| WO | 2018213209 A1 | 11/2018 |
| WO | 2022002054 A1 | 1/2022 |
| WO | 2023006048 A1 | 2/2023 |
| WO | 2023076103 A1 | 5/2023 |
| WO | 2023081236 A1 | 5/2023 |
| WO | 2023091769 A1 | 5/2023 |
| WO | 2023096804 A1 | 6/2023 |
| WO | 2023154250 A1 | 8/2023 |
| WO | 2023196150 A1 | 10/2023 |
| WO | 2023244454 A1 | 12/2023 |
| WO | 2023244767 A1 | 12/2023 |
| WO | 2023250114 A1 | 12/2023 |
| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

(56) References Cited

OTHER PUBLICATIONS

Pavcnik, M.D., Ph.D., Dusan, et al. "Development and Initial Experimental Evaluation of a Prosthetic Aortic Valve for Transcatheter Placement," Cardiovascular Radiology 1992; 183: 151-154.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Wheatley, M.D., David J., "Valve Prostheses," Rob & Smith's Operative Surgery, Fourth Edition, pp. 415-424, Butterworths 1986.
Bavaria, Joseph E. M.D. et al.: "Transcatheter Mitral Valve Implantation: The Future Gold Standard for MR?," Applicant requests the Examiner to consider this reference to be prior art as of December of 2010.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as June of 2014.
Bavaria, Joseph E. M.D.: "CardiAQ Valve Technologies: Transcatheter Mitral Valve Implantation," Sep. 21, 2009.
Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12): 1225-31, Applicant believes this may have been available as early as December of 2006.
Feldman, Ted, MD. "Prospects for Percutaneous Valve Therapies," Circulation 2007; 116:2866-2877. Applicant believes that this may be available as early as Dec. 11, 2007.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "'Double-Crowned Valved Stents For Off-Pump Mitral Valve Replacement," European Journal of Cardio-thoracic Surgery 28 (2005) 194-199, Applicant believes this may have been available as early as August of 2005.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on November of 2011 at TCT.
Ostrovsky, Gene, "Transcatheter Mitral Valve Implantation Technology from CardiAQ," medGadget, Jan. 15, 2010, available at: http://www.medgadget.com/2010/01/ transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies," Applicant believes this may have been presented on May 27, 2010 at EuroPCR.
Spillner, J. et al., "New Sutureless 'Atrial- Mitral-Valve Prosthesis' For Minimally Invasive Mitral Valve Therapy," Textile Research Journal, 2010, in 7 pages, Applicant believes this may have been available as early as Aug. 9, 2010.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"Company Overview," at TVT on Jun. 25, 2009.
Biospace, "CardiAQ Valve Technologies (CVT) Reports First-In-Human Percutaneous Transfemoral, Transseptal Implantation With Its Second Generation Transcatheter Bioprosthetic Mitral Heart

(56) References Cited

OTHER PUBLICATIONS

Valve," Jun. 23, 2015, p. 1, http://www.biospace.com/News/cardiaq-valve-technologies-cvt-reports-first- in/382370.

Biospace, "CardiAQ Valve Technologies (CVT) Reports Cardiovascular Medicine Milestone: First-In- Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

Neovasc corporate presentation, Oct. 2009, available at http://www.neovasc.com/investors/documents/Neovasc-Corporate-Presentation-Oct. 2009.pdf.

Herrmann., et al., "Advances in Transseptal Transcatheter Mitral Valve Replacement," Cardiovascular Research Foundation, tct2018, 10 Pages.

Medtronic: Transcatheter Aortic Valve Delivery Catheter System Compression Loading System, Core Valve Sytem, Medtronic Inc, 2014, pp. 1-61.

Neale, "Flushing TAVI Valves With Carbon Dioxide May Protect Against Brain Injury", EuroPCR 2023, May 16, 2023, 6 Pages.

\* cited by examiner

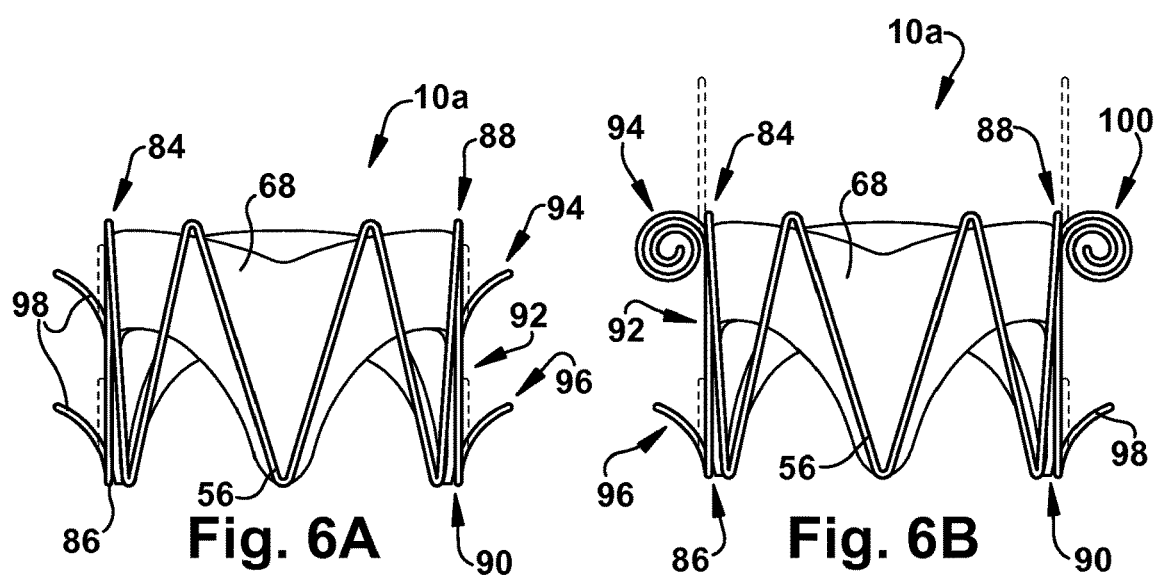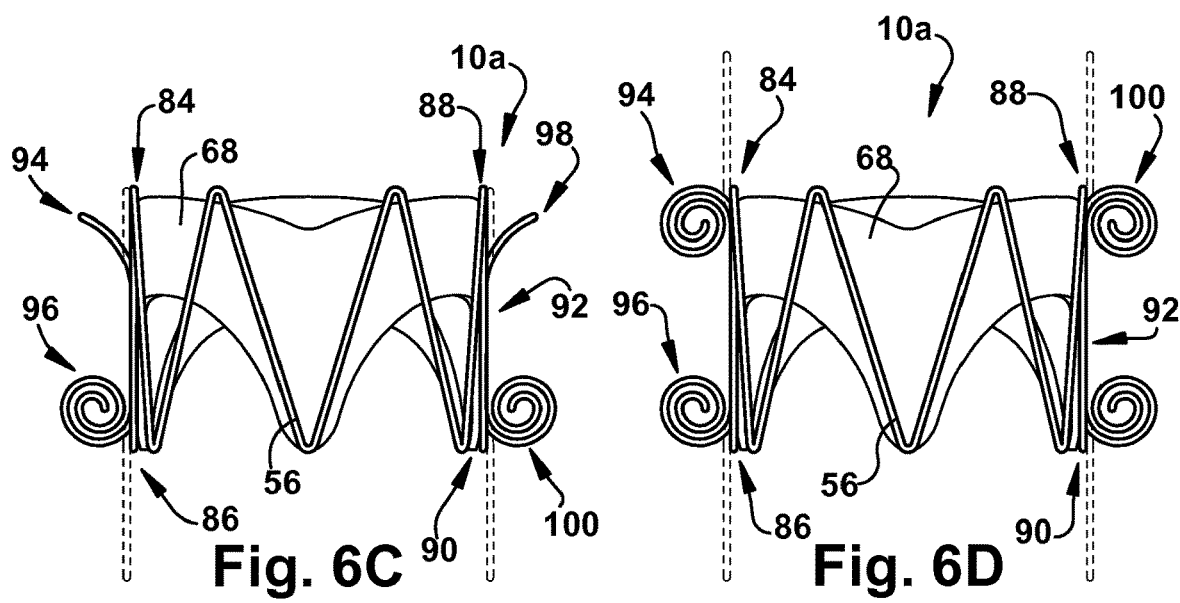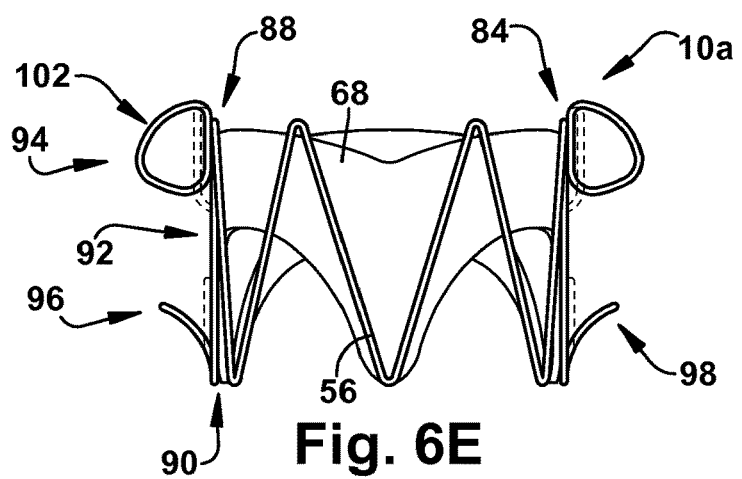

APPARATUS AND METHOD FOR REPLACING A DISEASED CARDIAC VALVE

RELATED APPLICATION

This application claims priority from U.S. Provisional Application No. 61/173,782, filed Apr. 29, 2009, the subject matter of which is incorporated herein by reference.

TECHNICAL FIELD

The present invention relates generally to apparatus and methods for treating heart disease, and more particularly to self-expandable apparatus and methods for treating diseased cardiac valves.

BACKGROUND OF THE INVENTION

There are two atrioventricular (AV) valves in the heart; one on the left side of the heart and one on the right side of the heart. The left side AV valve is the mitrel valve and the right side AV valve is the tricuspid valve. Both of these valves are subject damage and dysfunction that requires that the valve be repaired or replaced.

The mitrel and tricuspid valves differ significantly in anatomy. While the annulus of the mitrel valve is generally D-shaped, the annulus of the tricuspid valve is more circular. The effects of valvular dysfunction vary between the mitrel valve and the tricuspid valve. Mitrel valve regurgitation has more severe physiological consequences to the patient than does tricuspid valve regurgitation, a small amount of which is tolerable.

In mitrel valve insufficiency, the valve leaflets do not fully close and a certain amount of blood leaks back into the left atrium when the left ventricle contracts. As a result, the heart has to work harder by pumping not only the regular volume of blood, but also the extra volume of blood that regurgitated back into the left atrium. The added workload creates an undue strain on the left ventricle. This strain can eventually wear out the heart and result in morbidity. Consequently, proper function of the mitral valve is critical to the pumping efficiency of the heart.

Mitral and tricuspid valve disease is traditionally treated by either surgical repair with an annuloplasty ring or surgical replacement with a valve prosthesis. Surgical valve replacement or repair, however, is often an exacting operation. The operation requires the use of a heart-lung machine for external circulation of the blood as the heart is stopped and then opened during the surgical intervention. Once the heart is opened, the artificial cardiac valves and/or annuloplasty rings are sewed in under direct vision.

Surgical repair of the AV valves exposes patients (i.e., elderly patients) to many risks. A minimally invasive procedure that could be performed under local anesthesia in the cardiac catheterization lab, rather than in cardiac surgery, could therefore offer tremendous benefits to these patients. Consequently, an apparatus for replacing a diseased AV valve using a minimally invasive approach would be very helpful in providing additional opportunities to treat patients with valvular insufficiency and/or end stage heart failure.

SUMMARY OF THE INVENTION

According to one aspect of the present invention, an apparatus is provided for replacing a native cardiac valve. The native cardiac valve has at least one leaflet and is surrounded by a native cardiac valve annulus. The native cardiac valve annulus has a superior aspect and an inferior aspect. The apparatus comprises a barbell-shaped, expandable anchoring member including a first end portion, a second end portion, and a main body portion extending between the end portions. The main body portion includes a channel defined by an inner surface and an outer surface. Each of the first and second end portions has a diameter greater than the diameter of the main body portion. The first and second end portions are sized to respectively contact the superior and inferior aspects of the native cardiac valve annulus when the expandable anchoring member is in an expanded configuration. The apparatus also includes an expandable support member operably disposed within the main body portion of the expandable anchoring member, and a prosthetic cardiac valve secured within the expandable support member.

According to another aspect of the present invention, a method is provided for replacing a native cardiac valve. The native cardiac valve has at least one leaflet and is surrounded by a native cardiac valve annulus. The native cardiac valve annulus has a superior aspect and an inferior aspect. One step of the method comprises providing an apparatus including a barbell-shaped expandable anchoring member, an expandable support member, and a prosthetic cardiac valve secured within the expandable support member. The expandable support member is secured within the expandable anchoring member. Each of the first and second end portions has a diameter greater than the diameter of the main body portion. The apparatus is placed into a delivery catheter, and the delivery catheter inserted into an atrial chamber. The delivery catheter is advanced until the delivery catheter is positioned within the native cardiac valve annulus. Next, the apparatus is removed from the delivery catheter so that the expandable anchoring member obtains an expanded configuration and the first and second end portions of the expandable anchoring member respectively contact the superior and inferior aspects of the native cardiac valve annulus and thereby secure the expandable anchoring member in the native cardiac annulus.

According to another aspect of the present invention, an apparatus is provided for replacing a native cardiac valve. The native cardiac valve has at least one leaflet and is surrounded by a native cardiac valve annulus. The native cardiac valve annulus has a superior aspect and an inferior aspect. The apparatus comprises an expandable support member, a prosthetic cardiac valve operably secured within the expandable support member, and a securing member operably connected to the expandable support member. The securing member comprises an elongated body member having a first end, a second end, and a main body portion extending between the first and second ends. The second end includes a first attachment member operably connected thereto for contacting the inferior aspect of the native cardiac valve annulus when the expandable support member is in an expanded configuration.

According to another aspect of the present invention, a method is provided for replacing a native cardiac valve. The native cardiac valve has at least one leaflet and is surrounded by a native cardiac valve annulus.

The native cardiac valve annulus has a superior aspect and an inferior aspect. One step of the method comprises providing an apparatus including an expandable support member having a prosthetic cardiac valve secured therein and a securing member operably connected to the expandable support member. The securing member comprises an elongated body member having a first end, a second end, and a main body portion extending between the first and second ends. The second end includes a first attachment member operably connected thereto. The expandable anchoring member is placed into a delivery catheter, and the delivery catheter is then inserted into an atrial chamber. The delivery catheter is advanced until the delivery catheter is positioned within the native cardiac valve annulus. Next, the apparatus is removed from the delivery catheter so that the expandable support member obtains an expanded configuration and the first attachment member of the securing member contacts the inferior aspect of the native cardiac valve annulus and thereby secures the expandable support member in the native cardiac valve annulus.

According to another aspect of the present invention, an apparatus is provided for replacing a native cardiac valve. The native cardiac valve has at least one leaflet and is surrounded by a native cardiac valve annulus. The native cardiac valve annulus has a superior aspect and an inferior aspect. The apparatus comprises a securing member including an elongated body member having a first end, a second end, and a main body portion extending between the first and second ends. The second end includes a first attachment member operably connected thereto for contacting the inferior aspect of the native cardiac valve annulus when the expandable support member is in an expanded configuration. The apparatus also comprises a prosthetic valve operably secured to the securing member.

According to another aspect of the present invention, a method is provided for replacing a native cardiac valve. The native cardiac valve has at least one leaflet and is surrounded by a native cardiac valve annulus. The native cardiac valve annulus has a superior aspect and an inferior aspect. One step of the method includes providing an apparatus comprising a securing member and a prosthetic cardiac valve operably connected to the securing member. The securing member comprises an elongated body member having a first end, a second end, and a main body portion extending between the first and second ends. The second end includes a first attachment member operably connected thereto for contacting the inferior aspect of the native cardiac valve annulus when the expandable support member is in an expanded configuration. The apparatus is placed into a delivery catheter, and the delivery catheter is then inserted into an atrial chamber. The delivery catheter is advanced until the delivery catheter is positioned within the native cardiac valve annulus. Next, the apparatus is removed from the delivery catheter so that the prosthetic cardiac valve expands in place of the native cardiac valve and the first attachment member of the securing member contacts the inferior aspect of the native cardiac valve annulus and thereby secures the prosthetic cardiac valve in the native cardiac valve annulus.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6A is a cross-sectional view showing another alternative embodiment of the apparatus in FIG. 1C;

FIG. 6B is a cross-sectional view showing an alternative embodiment of the apparatus in FIG. 6A;

FIG. 6C is a cross-sectional view showing another alternative embodiment of the apparatus in FIG. 6A;

FIG. 6D is a cross-sectional view showing another alternative embodiment of the apparatus in FIG. 6A;

FIG. 6E is a cross-sectional view showing another alternative embodiment of the apparatus in FIG. 6A;

FIG. 1C is a cross-sectional view showing the apparatus of FIG. 9 implanted in a native mitral valve;

DETAILED DESCRIPTION

The present invention relates generally to apparatus and methods for treating heart disease, and more particularly to self-expandable apparatus and methods for treating diseased cardiac valves. As representative of the present invention, FIGS. 1A-E illustrate one embodiment of an apparatus 10 for replacing a native cardiac valve. Although the present invention is described herein as being useful for treating a diseased mitral valve, it should be appreciated that other cardiac valves, such as the tricuspid valve, the pulmonary valve, and the aortic valve are also treatable according to the present invention.

Figure 2:
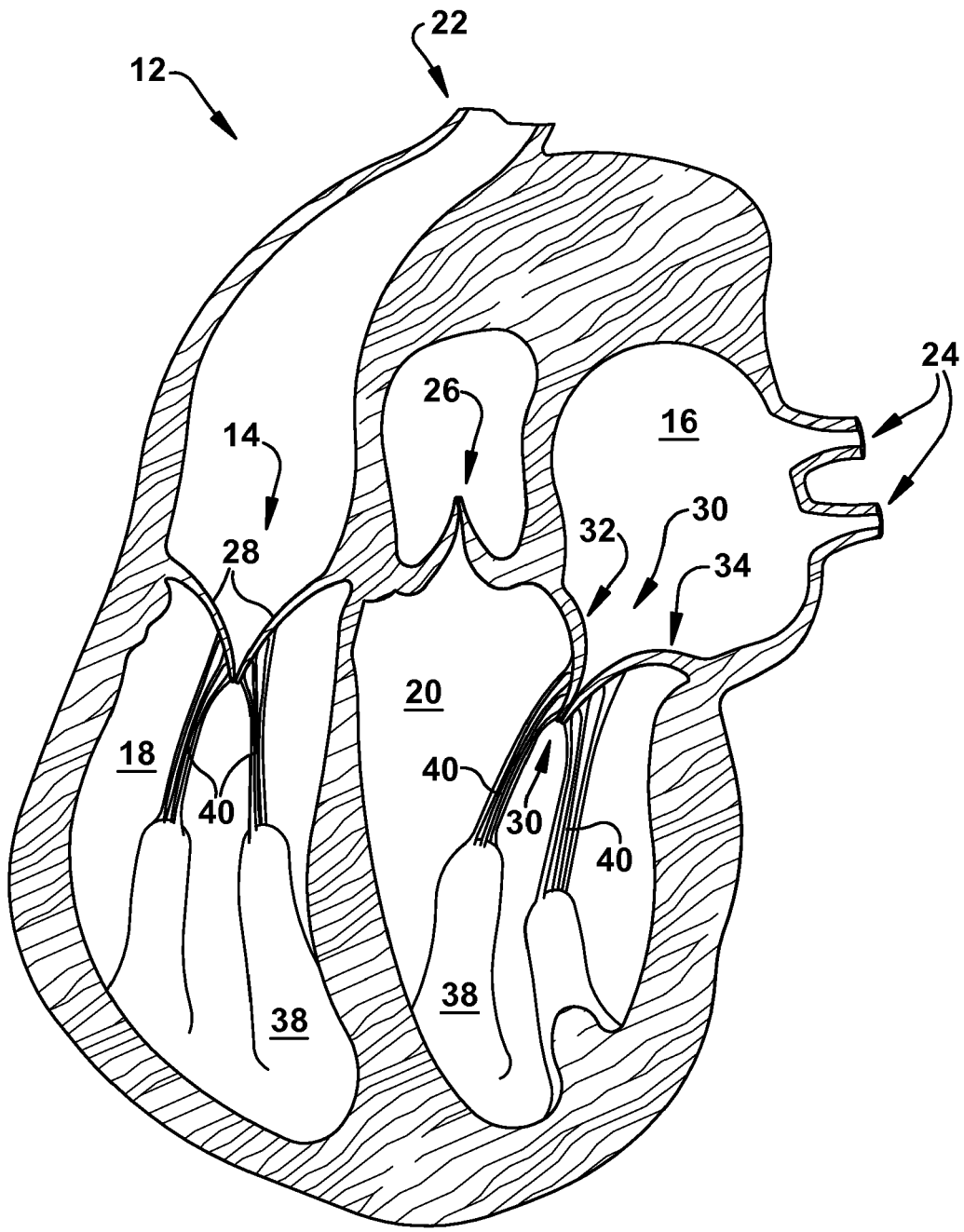
FIG. 2 is a cross-sectional view of a human heart.

FIG. 2 shows a human heart 12. The human heart 12 contains four chambers: the right and left atria 14 and 16 and the right and left ventricles 18 and 20. The thin-walled right atrium 14 receives deoxygenated blood from the superior vena cava 22, the inferior vena cava (not shown), and from the coronary sinus (not shown). The thin-walled left atrium 16 receives oxygenated blood from pulmonary veins 24. The right and left ventricles 18 and 20 pump oxygenated and deoxygenated blood, respectively, throughout the body, and the pocket-like pulmonary (not shown) and aortic 26 semi-lunar valves prevent reflux into the ventricles.

Atrial blood is pumped through the atrioventricular orifices, guarded by the 3-cusp tricuspid valve 28 on the right and the 2-cusp mitral valve 30 on the left. The mitral valve 30 is formed by two leaflets; namely, the anterior leaflet 32 and the posterior leaflet 34. The anterior leaflet 32 extends along a generally planar base of a D-shaped mitral annulus 36 (FIG. 5), while the posterior leaflet 34 (FIG. 2) extends arcuately around the curved portion of the annulus. The mitrel and tricuspid valves 28 and 30 are secured to the papillary muscles 38 in the right and left ventricles 18 and 20 by tendinous chordae tendineae 40, and by the mitral annulus 36 and the tricuspid annulus (not shown in detail).

Figure 1A:
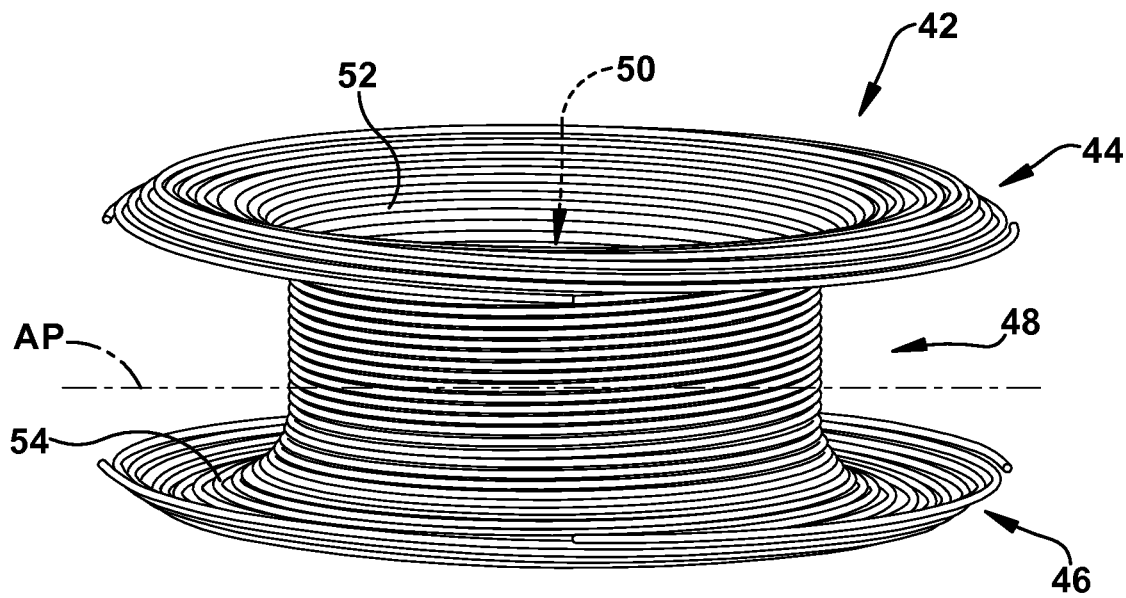
FIG. 1A is a perspective view of an expandable anchoring member constructed in accordance with the present invention.

Referring again to FIGS. 1A-E, one embodiment of the present invention includes an apparatus 10 for replacing a native cardiac valve, such as a native mitral valve 30. As shown in FIG. 1A, the apparatus 10 comprises a barbell-shaped expandable anchoring member 42. The expandable anchoring member 42 includes a first end portion 44, a second end portion 46, and a main body portion 48 extending between the first and second end portions. The main body portion 48 includes a channel 50 defined by an inner surface 52 and an outer surface 54. The main body portion 48 has a generally cylindrical shape and is adapted to conform to the three-dimensional shape of a native cardiac valve annulus. It will be appreciated that the size and shape of the main body portion 48 may be varied as needed. For example, the diameter, circumference, and/or length of the main body portion 48 may be varied so that the expandable anchoring member 42 more readily conforms to the shape of a native cardiac valve annulus.

Figure 3A:
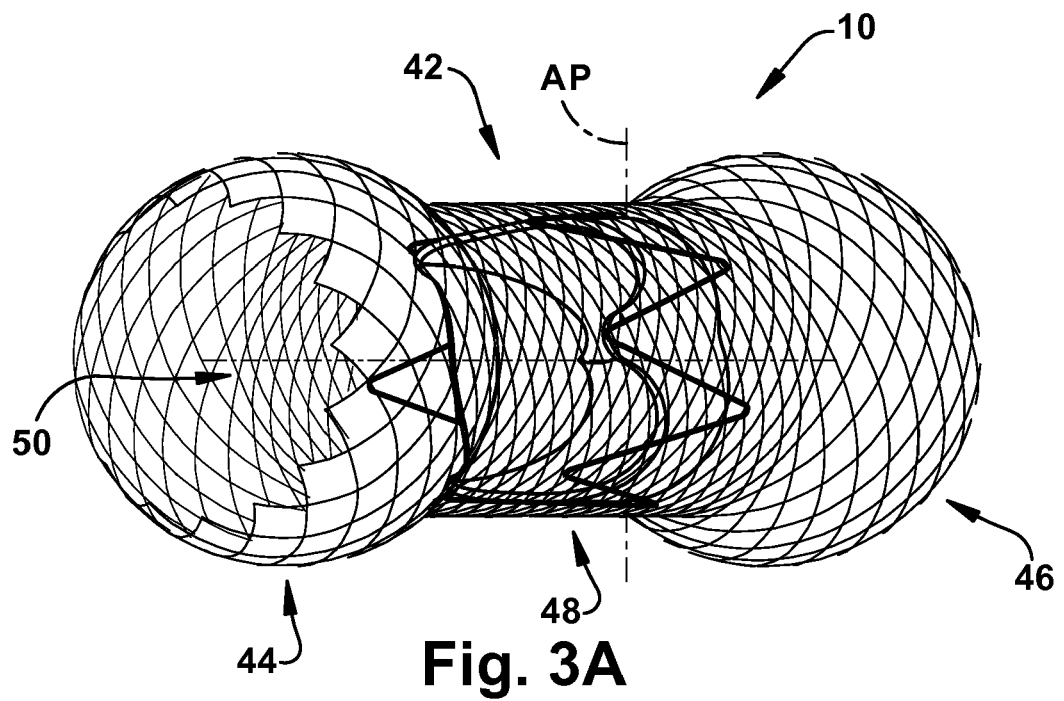
FIG. 3A is a perspective view showing an alternative embodiment of the expandable anchoring member in FIG. 1A.
Figure 3B:
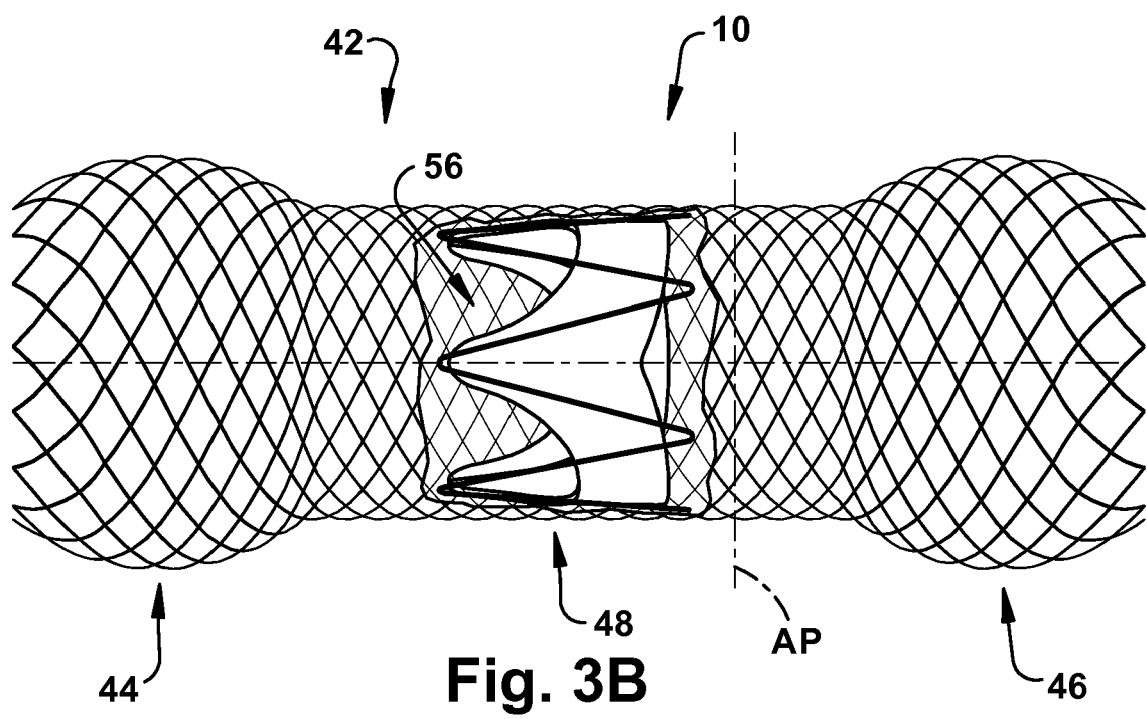
FIG. 3B is a perspective view showing an alternative embodiment of the apparatus in FIG. 1C.

Each of the first and second end portions 44 and 46 of the expandable anchoring member 42 has a diameter that is greater than the diameter of the main body portion 48. As described in more detail below, the first and second end portions 44 and 46 are sized to respectively contact the superior and inferior aspects of a native cardiac valve annulus when the expandable anchoring member 42 is in an expanded configuration. The first and second end portions 44 and 46 can have identical or different configurations. As shown in FIG. 1A, for example, the first and second end portions 44 and 46 have a hemi-spherical shape with respect to an axial plane AP of the main body portion 48. Alternatively, the first and second end portions 44 and 46 of the expandable anchoring member 42 can have bulbous shape (FIGS. 3A-B).

The expandable anchoring member 42 is comprised of a single strand of a flexibly resilient material, such as Nitinol, stainless steel, or other suitable medical grade metals or plastics having shape memory characteristics. It will be appreciated, however, that the expandable anchoring member 42 can alternatively be comprised of multiple strands. Additionally, at least a portion of the expandable anchoring member 42 may be made from a bioabsorbable material including, for example, magnesium alloy, dendrimers, biopolymers such as thermoplastic starch, polyalctides, cellulose, and aliphatic aromatic copolyesters. The expandable anchoring member 42 may also be made of a radio-opaque material or include radio-opaque markers (not shown) to facilitate fluoroscopic visualization. The flexible and expandable properties of the expandable anchoring member 42 facilitate delivery of the apparatus 10 to a diseased native cardiac valve.

Figure 1B:
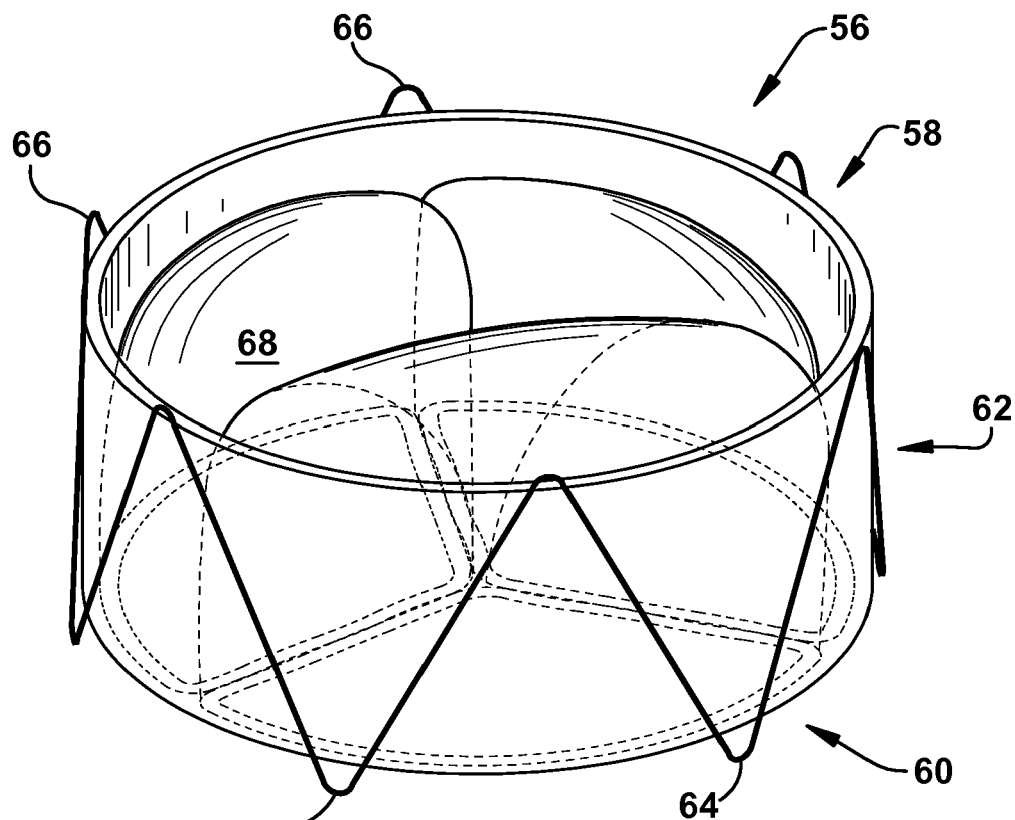
FIG. 1B is a perspective view of a prosthetic valve operably secured to an expandable support member.

The apparatus 10 (FIG. 1C) additionally includes an expandable support member 56 (FIG. 1B) operably disposed within the main body portion 48 of the expandable anchoring member 42. The expandable support member 56 can be secured within the main body portion 48 using any one or combination of known fastening means (not shown), such as sutures, clips, pins, staples, adhesives, or the like. As shown in FIG. 1B, the expandable support member 56 includes oppositely disposed proximal and distal end portions 58 and 60, and a main body portion 62 extending between the end portions. The expandable support member 56 is both flexible and resilient and, as discussed in more detail below, can be made of a shape memory material such as Nitinol, stainless steel, or other suitable medical grade metals or plastics having shape memory characteristics.

The expandable support member 56 may additionally or optionally be made from a bioabsorbable material including, for example, magnesium alloy, dendrimers, biopolymers such as thermoplastic starch, polyalctides, cellulose, and aliphatic aromatic copolyesters. The expandable support member 56 may also be made of a radio-opaque material or include radio-opaque markers to facilitate fluoroscopic visualization. The flexible and expandable properties of the expandable support member 56 facilitate placement and movement of the expandable support member within the main body portion 48 of the expandable anchoring member 42.

The expandable support member 56 comprises a continuous series of W-shaped segments which collectively form a mesh-like configuration. It is contemplated, however, that other geometries may be used. The lower tips 64, as viewed in FIG. 1B, of the W-shaped segments form the distal end portion 60 of the expandable support member 56, and the upper tips 66 of the W-shaped segments form the proximal end portion 58 of the expandable support member. Other examples of expandable support members 56 which may be used as part of the present invention are disclosed in U.S. Patent Pub. No. 2007/0255389 A1, the entirety of which is hereby incorporated by reference.

As shown in FIGS. 1B-E, the expandable support member 56 also includes a prosthetic valve 68 operably secured therein. The prosthetic valve 68 is secured to the expandable support member 56 using any one or combination of known fastening means (not shown), such as sutures, pins, clips, staples, adhesives, or the like. Examples of prosthetic valves 68 are known in the art and can include, for instance, the prosthetic valves disclosed in U.S. Pat. No. 5,156,621, which is hereby incorporated by reference in its entirety.

The prosthetic valve 68 may be fixed and preserved using a variety of known methods. The use of chemical processes for the fixation and preservation of biological tissues have been described and are readily available in the art. For example, glutaraldehyde and other related aldehydes have seen widespread use in preparing cross-linked biological tissues. Glutaraldehyde is a five carbon aliphatic molecule with an aldehyde at each end of the chain, rendering it bifunctional. These aldehyde groups react under physiological conditions with primary amine groups on collagen molecules resulting in the cross-linking of collagen containing tissues. Methods for glutaraldehyde fixation of biological tissues have been extensively described and are well known in the art. In general, a biological tissue sample to be cross-linked is simply contacted with a glutaradeyde solution for a duration effective to cause the desired degree of cross-linking within the biological tissue being treated.

Many variations and conditions have been applied to optimize glutaraldehyde fixation procedures. For example, lower concentrations have been found to be better in bulk tissue cross-linking compared to higher concentrations. It has been proposed that higher concentrations of glutaraldehyde may promote rapid surface cross-linking of the tissue, generating a barrier that impedes or prevents the further diffusion of glutaradehdye into the tissue bulk. For most bioprosthesis applications, however, the tissue is treated with a relatively low concentration glutaraldehyde solution, e.g., typically between 0.1%-5%, for 24 hours or more to ensure optimum fixation. Various other combinations of glutaraldehyde concentrations and treatment times will also be suitable depending on the objectives for a given application. Examples of such other combinations include, but are not limited to, those disclosed in U.S. Pat. Nos. 6,547,827, 6,561,970, and 6,878,168, all of which are hereby incorporated by reference in their entireties.

In addition to bifunctional aldehydes, many other chemical fixation procedures have been described. For example, some methods have employed polyethers, polyepoxy compounds, diisocyanates, and azides. These and other approaches are available to the skilled artisan for treating biological tissues, and are suitable for cross-linking vascular graft tissue according to the present invention.

The prosthetic valve 68 may also be treated and preserved with a dry tissue valve procedure as described in U.S. Pat. No. 6,534,004, the entire contents of which are hereby incorporated by reference. Furthermore, the prosthetic valve 68 may be treated with anti-calcification solutions, such as XenoLogiX® treatment (Edwards Lifesciences, Irvine, CA), the SynerGraf® (CryoLife, Inc., Kennesaw, GA) treatment process, and/or anti-calcification agents, such as a-amino oleic acid.

The apparatus 10 may further include a layer (not shown) of biocompatible material covering at least a portion of the expandable anchoring member. The layer of biocompatible material may be synthetic, such as Dacron® (Invista, Wichita, KS), woven velour, polyurethane, polytetrafluoroethylene (PTFE), expanded PTFE, Gore-Tex® (W. L. Gore & Associates, Flagstaff, AZ), or heparin-coated fabric. Alternatively, the layer may be a biological material, such as bovine or equine pericardium, peritoneal tissue, an allograft, a homograft, a patient graft, or a cell-seeded tissue. The layer can cover either the inner surface 52 of the expandable anchoring member 42, the outer surface 54 of the expandable anchoring member, or a combination thereof. The layer may be attached around the entire circumference of the expandable anchoring member 42 or, alternatively, may be attached in pieces or interrupted sections to allow the expandable anchoring member to more easily expand and contract. By covering a portion of the expandable anchoring member 42 with a layer of biocompatible material, the hemocompatibility of the apparatus 10 may be improved.

At least a portion of the apparatus 10 may be treated with a therapeutic agent for eluting into cardiac tissue and/or blood. The therapeutic agent may be capable of treating a variety of pathological conditions including, but not limited to, thrombosis, stenosis and inflammation. Accordingly, the therapeutic agent may include at least one of an anticoagulant, an antioxidant, a fibrinolytic, a steroid, an anti-apoptotic agent, an anti-inflammatory agent, a receptor agonist or antagonist, and/or a hormone.

Optionally or additionally, the therapeutic agent may be capable of treating or preventing other diseases or disease processes, such as microbial infections. In these instances, the therapeutic agent may include an anti-microbial agent and/or a biological agent such as a cell, peptide or nucleic acid. The therapeutic agent can be simply linked to a surface of the apparatus 10, embedded and released from within polymer materials, such as a polymer matrix, or surrounded by and released through a carrier. The entire apparatus 10, or only a portion thereof, may be treated with the therapeutic agent. Additionally, different portions of the apparatus 10 may be treated with different therapeutic agents.

Figure 4:
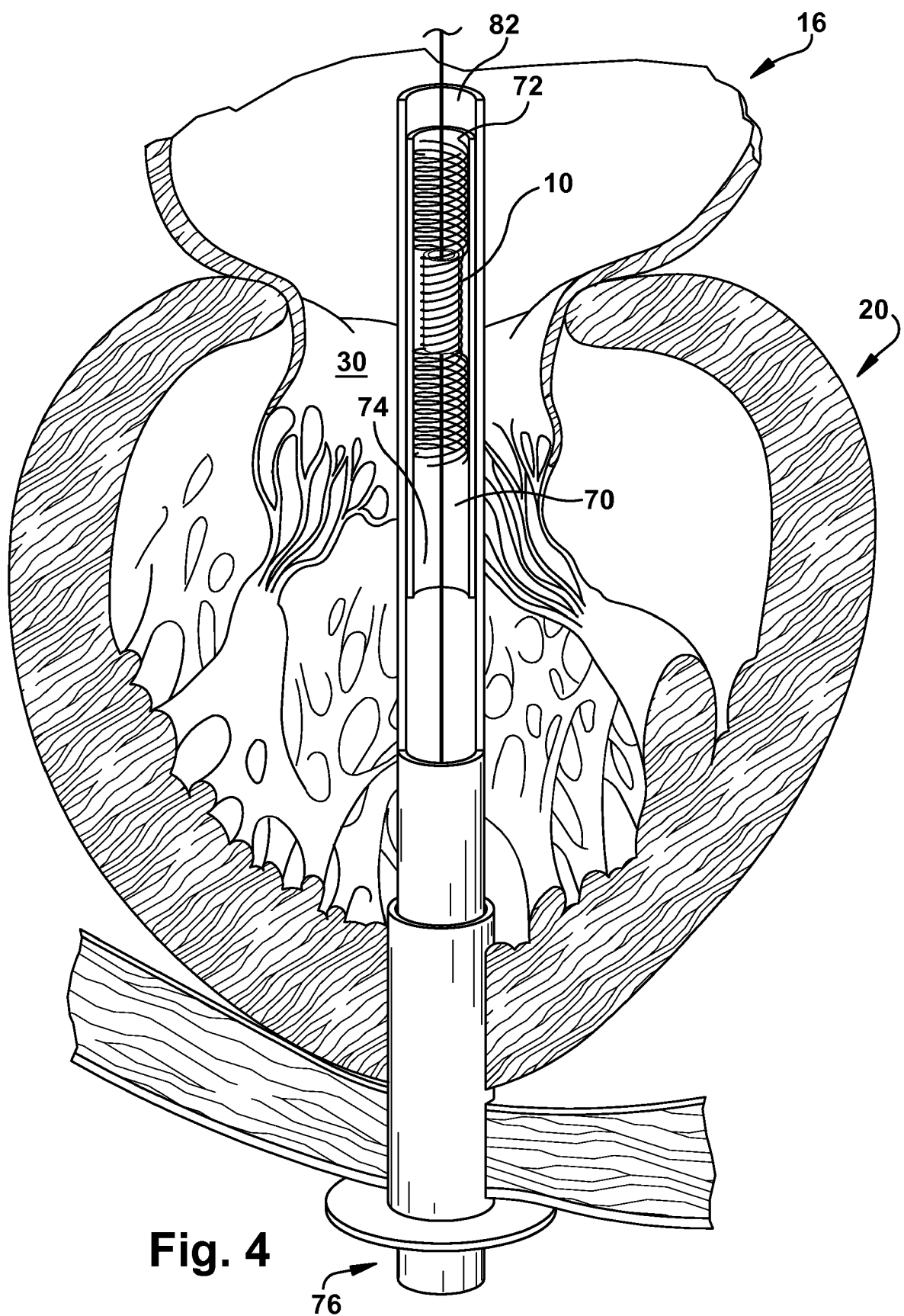
FIG. 4 is a perspective view showing the apparatus of FIG. 1C being delivered to a native mitral valve.
Figure 5:
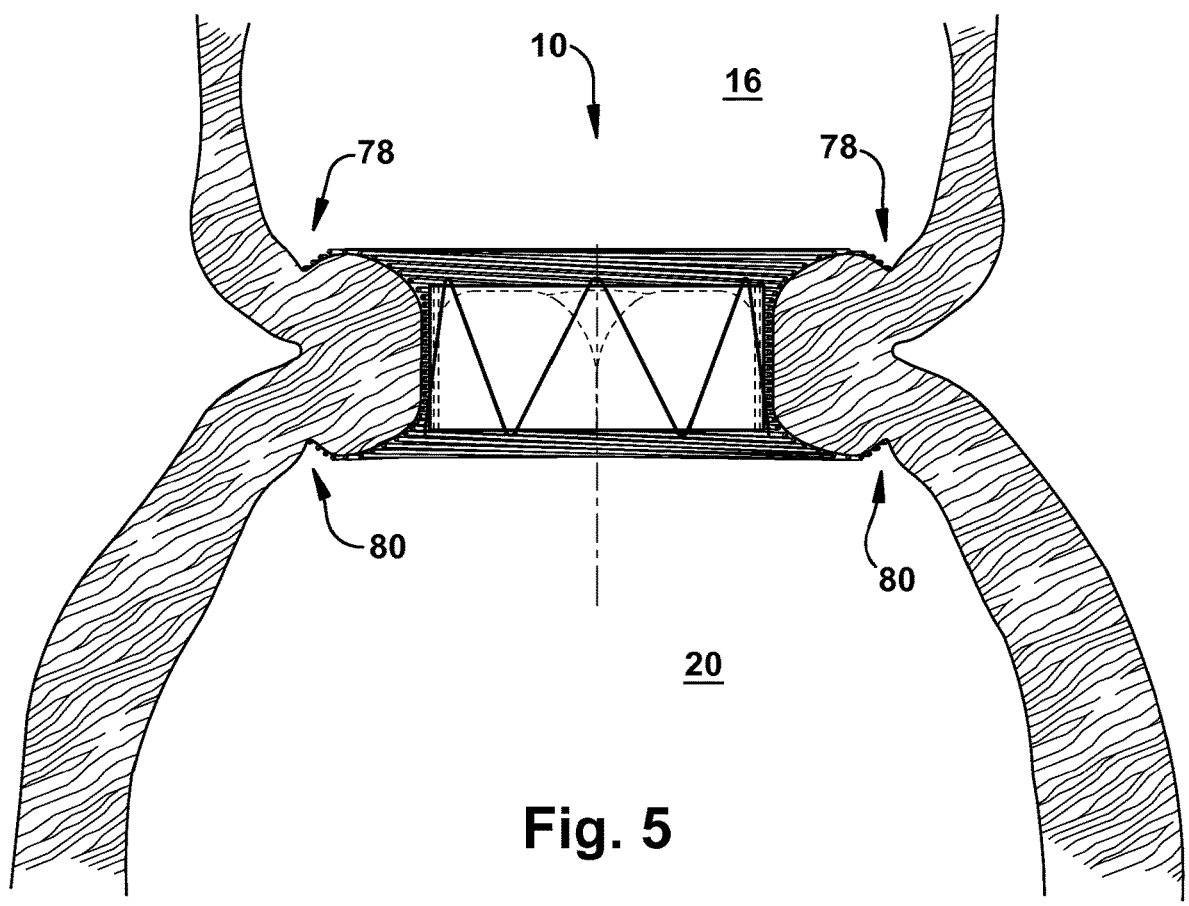
FIG. 5 is a cross-sectional view showing the apparatus of FIG. 1C implanted in a native mitral valve.

The apparatus 10 shown in FIGS. 1A-E and FIGS. 3A-B can be used to replace a diseased mitral valve 30, for example, using any one or combination of known surgical methods. As shown in FIGS. 4-5, for example, an apical puncture method can be used to respectively deliver the apparatus 10 shown in FIG. 1C. It will be appreciated, however, that other percutaneous, transvascular, and/or open surgical procedures may be used to deliver the apparatus 10 to a diseased cardiac valve. For example, the apparatus 10 can be delivered to the tricuspid valve 28 via the pulmonary artery (not shown) or to the mitral valve 30 via the aortic valve 26. It will also be appreciated that the method of the present invention will typically entail gaining access to a beating heart 12; however, the present invention may also be used for intravascular stopped-heart access as well as stopped-heart open chest procedures.

Figure 1C:
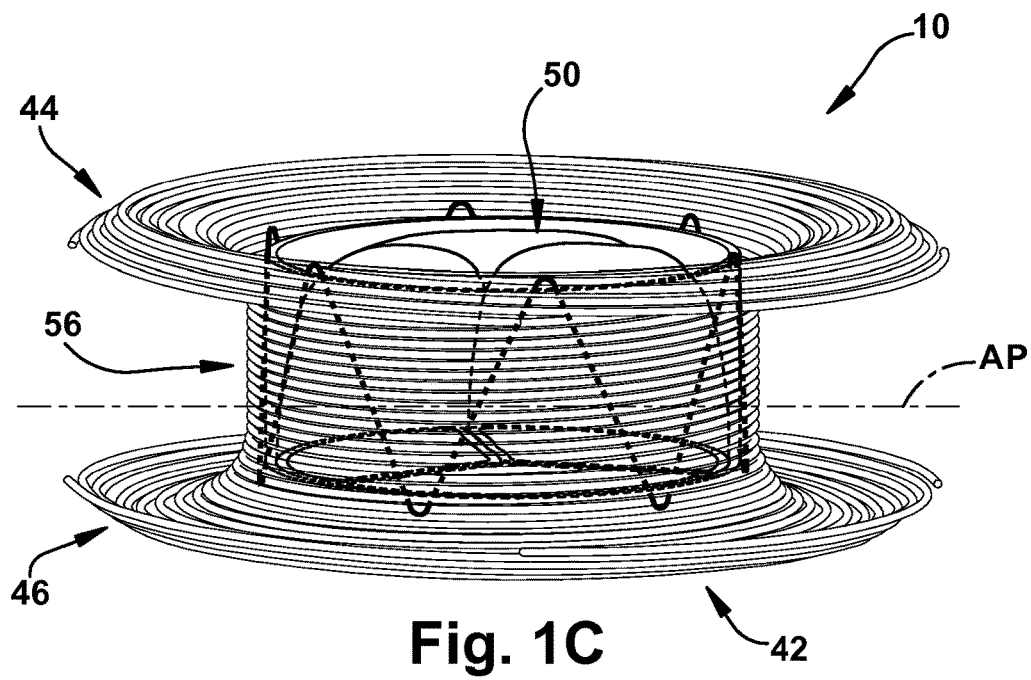
FIG. 1C is a perspective view of an apparatus for replacing a native cardiac valve constructed in accordance with the present invention.
Figure 1D:
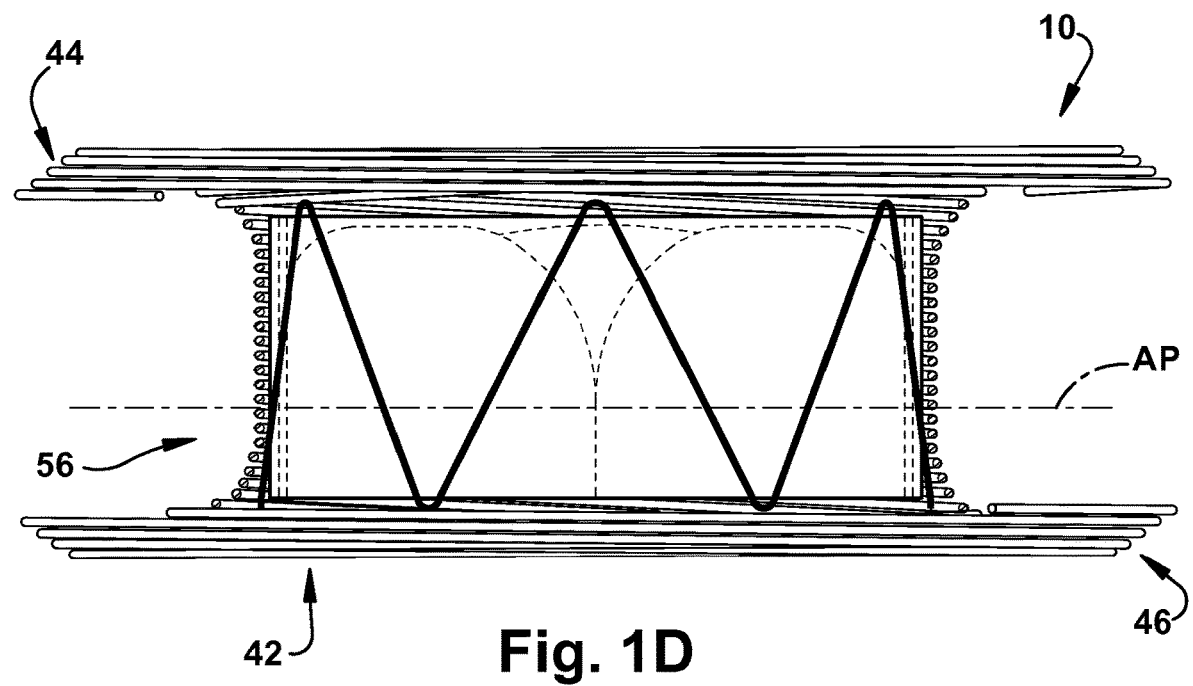
FIG. 1D is a cross-sectional view of the apparatus shown in FIG. 1C.
Figure 1E:
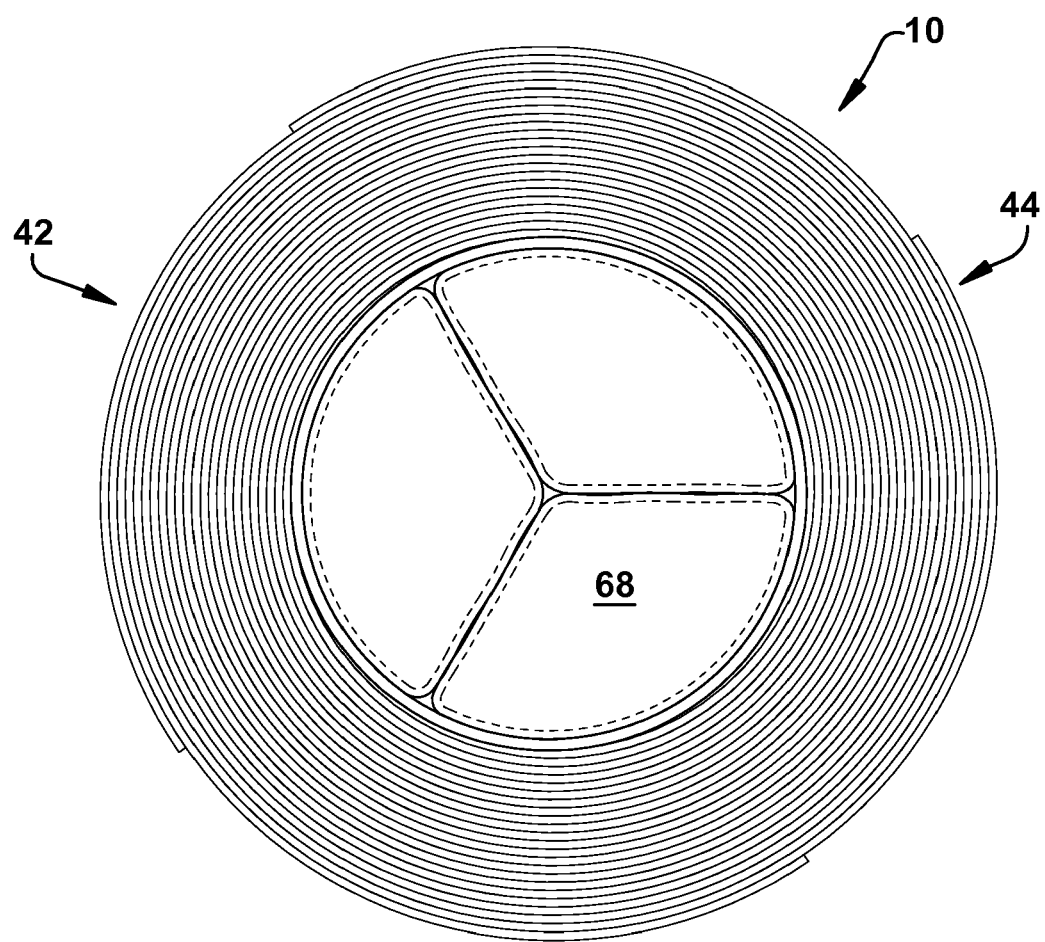
FIG. 1E is a top plan view of the apparatus shown in FIG. 1C.

FIG. 4 illustrates one step of an apical puncture method for delivering the apparatus 10 shown in FIG. 1C to a native cardiac valve, such as the mitral valve 30. One step of the method includes placing the apparatus 10 into a delivery catheter 70. As shown in FIG. 4, the delivery catheter 70 has proximal end portion 72 and a distal end portion 74. The delivery catheter 70 is shaped to facilitate insertion and removal of the apparatus 10 into and out of a puncture tool 76 (not shown in detail). The delivery catheter 70 may be constructed from a rigid, semi-rigid, or flexible material. For example, the delivery catheter 70 may be made of a flexible elastic material, such as a shape memory alloy, a super-elastic material (e.g., Nitinol, spring stainless steel, etc.), or plastic. Alternatively, the delivery catheter 70 may be made of a rigid material, such as hardened plastic, silicon, polyurethane, or the like.

Prior to placing the apparatus 10 into the delivery catheter 70, the dimensions of the native mitral valve 30 and the native mitral annulus 36 are determined. Various methods and devices for determining the dimensions of cardiac valves and cardiac valve annuluses are known in the art and include, for example, echocardiogram, computed tomography, magnetic resonance imaging, fluoroscopy, and angiography. After determining the dimensions of the native mitral valve 30 and the native mitral annulus 36, an appropriately-sized apparatus 10 is chosen for implantation. For example, the main body portion 48 of the expandable anchoring member 42 can be appropriately-sized so that the diameter of the main body portion corresponds to the diameter of the native mitral annulus 36. Additionally, the first and second end portions 44 and 46 of the expandable anchoring member 42 can also be appropriately-sized so that the first and second end portions respectively contact the superior and inferior aspects 78 and 80 of the mitral annulus 36 when the expandable anchoring member is in an expanded configuration.

After selecting an appropriately-sized apparatus $10_a$ the puncture tool 76 is used to puncture the chest wall and extend through the apical portion of the left ventricle 20 into the left ventricular chamber. The delivery catheter 70 is then urged through the puncture tool 76 as shown in FIG. 4 so that the delivery catheter is positioned at a distal end portion 82 of the puncture tool. Both the puncture tool 76 and the delivery catheter 70 are then progressively withdrawn so that the first end portion 44 of the expandable anchoring member 42 expands to contact the superior aspect 78 of the native mitral annulus 36. Once the delivery catheter 70 and the puncture tool 76 have been completely withdrawn from the left ventricle 20, the main body portion 48 and the second end portion 46 of the expandable anchoring member 42 expand into the native mitral annulus 36 (FIG. 5). With the apparatus 10 securely positioned in the native mitral annulus 36, normal blood flow can resume through the prosthetic valve 68.

Another embodiment of the present invention is illustrated in FIGS. 6A-E. The apparatus $10_a$, is identically constructed as the apparatus 10 shown in FIGS. 1A-E, except where as described below. In FIGS. 6A-E, structures that are identical as structures in FIGS. 1A-E use the same reference numbers, whereas structures that are similar but not identical carry the suffix "a".

An apparatus $10_a$ for replacing a native cardiac valve, such as a native mitral valve 30 can comprise an expandable support member 56 and a prosthetic cardiac 68 valve operably secured within the expandable support member. As shown in FIGS. 6A-E, the apparatus $10_a$, can further include a securing member 84 operably connected to the expandable support member 56. The securing member 84 can comprise an elongated body member 86 having a first end 88, a second end 90, and a main body portion 92 extending between the first and second ends. The securing member 84 can be operably secured to the expandable support member 56 using any one or combination of known fastening means (not shown), such as sutures, clips, pins, staples, adhesives, or the like.

The second end 90 of the elongated body member 84 can include a first attachment member 94 operably connected thereto for contacting the inferior aspect of the native cardiac valve annulus when the expandable support member 56 is in an expanded configuration. As shown in FIGS. 6A-E, the first end 88 of the elongated body member 86 can also include a second attachment member 96 operably connected thereto for contacting the superior aspect of the native cardiac valve annulus when the expandable support member 56 is in an expanded configuration. The first and second attachment members 94 and 96 can be made from any one or combination of flexibly resilient, medical grade materials, including, for example, Nitinol, stainless steel, or other suitable metals or plastics having shape memory characteristics.

The first and second attachment members 94 and 96 can have a variety of configurations. As shown in FIGS. 6A-C, for example, the first and second attachment members 94 and 96 can include flexible, rod-shaped members 98. The rod-shaped members 98 can be joined to or integrally formed with the elongated body member 86 so that the rod-shaped members can transition from a collapsed configuration (indicated by the dashed lines) to an expanded configuration. In the collapsed configuration, the rod-shaped members 98 can extend substantially parallel to the elongated body member 86. In the expanded configuration, the rod-shaped members 98 can extend substantially axial to the elongated body member 86. As described in more detail below, the rod-shaped members 98 located at the first and second ends 88 and 90 of the elongated body member 86 can respectively contact the superior and inferior aspects 78 and 80 of the mitral annulus 36 when the apparatus $10_a$ is in an expanded configuration.

As shown in FIGS. 6B-D, the first and second attachment members 94 and 96 can also comprise a windable coil 100. The windable coil 100 can be made of a flexible wire or rod capable of transitioning between an expanded configuration and a collapsed configuration. In the expanded configuration (indicated by the dashed lines), the windable coil 100 can obtain a substantially linear configuration so that the windable coil extends substantially parallel to the elongated body member 86. In the collapsed configuration (FIGS. 6B-D), the windable coil 100 can obtain a substantially circular configuration and extend substantially axial to the elongated body member 86. As described in more detail below, each of the windable coils 100 located at the first and second ends 88 and 90 of the elongated body member 86 can respectively contact the superior and inferior aspects 78 and 80 of a native mitral annulus 36 when the apparatus $10_a$ is in an expanded configuration.

The first and second attachment members 94 and 96 can additionally comprise an anchoring ring 102 (FIG. 6E). The anchoring ring 102 can be similarly or identically constructed as the first and second end portions 44 and 46 of the expandable anchoring member 42 shown in FIGS. 3A-B. In an expanded configuration, the anchoring ring 102 can have a bulbous shape and extend substantially axial to the elongated body member 86. In a collapsed configuration (indicated by dashed lines), the anchoring ring 102 can extend substantially parallel to the elongated body member 86. The anchoring ring 102 can be made of a flexible, mesh-like material having shape memory characteristics.

Figure 7:
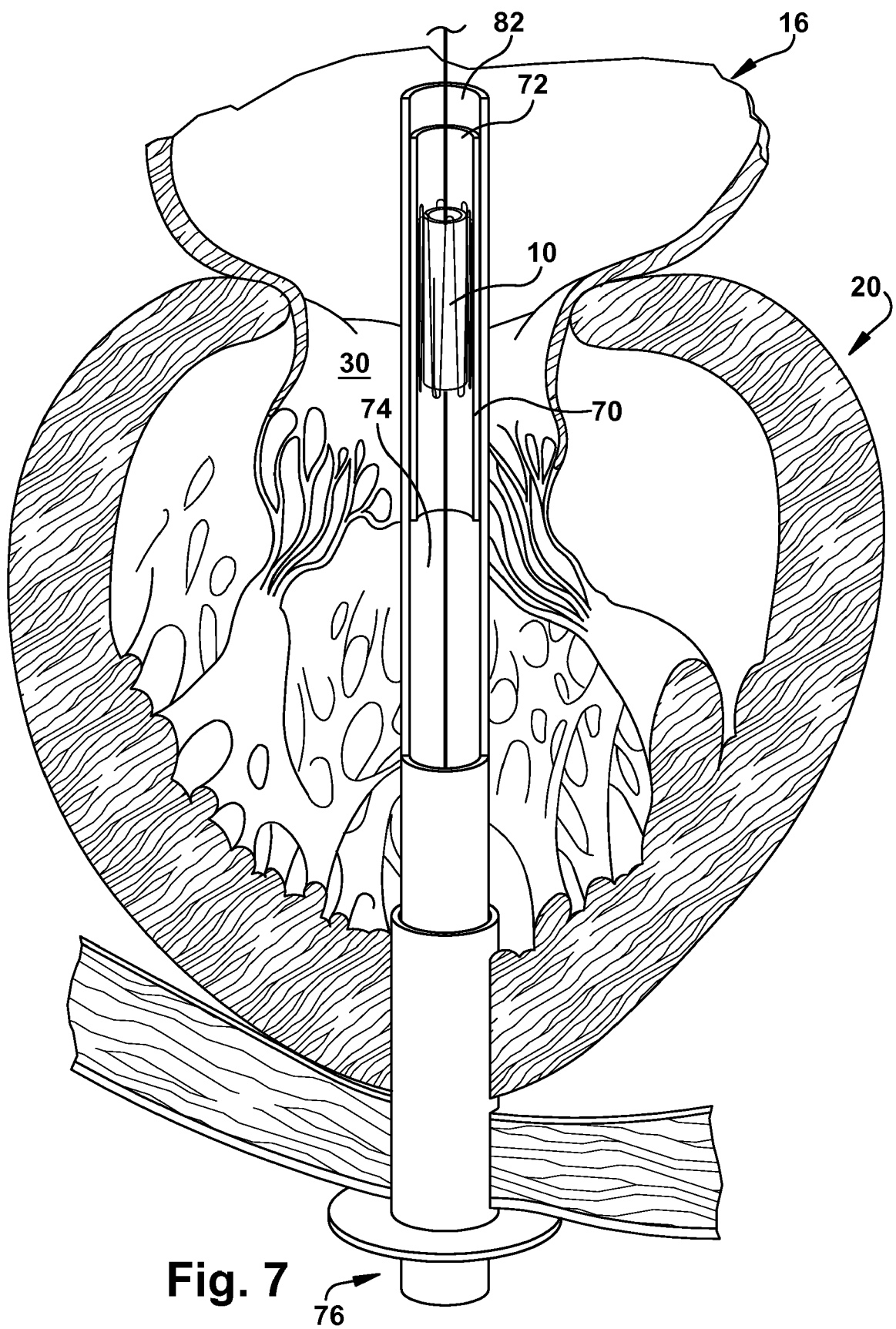
FIG. 7 is a perspective view showing the apparatus of FIG. 6A being delivered to a native mitral valve.
Figure 8:
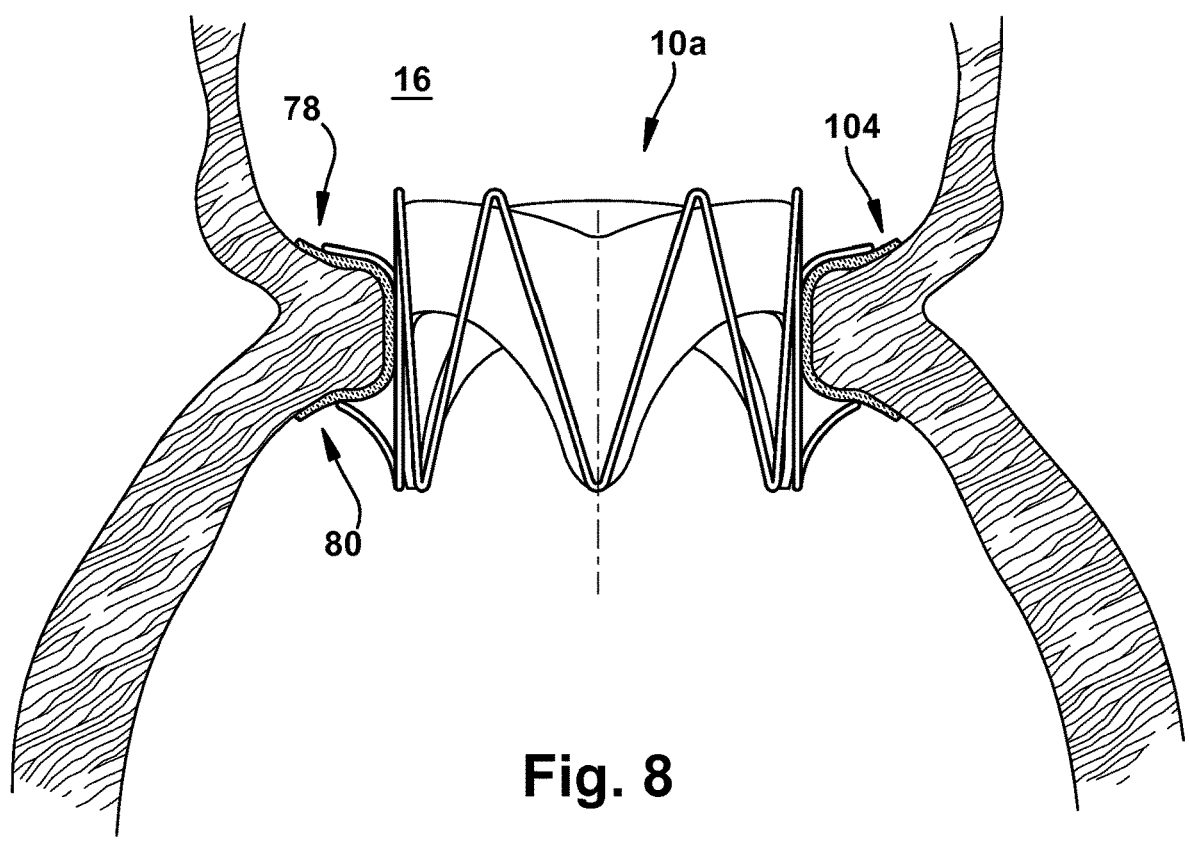
FIG. 8 is a cross-sectional view showing the apparatus of FIG. 6A implanted in a native mitral valve.

It will be appreciated that the apparatus $10_a$ shown in FIGS. 6A-E can additionally include a layer 104 (FIG. 8) of material that extends around all or a portion of the expandable support member 56. The layer 104 of material can be made of any one or combination of known biocompatible materials, some of which are described above. For example, the layer 104 can be made of PTFE or ePTFE. The layer 104 of material can function as a seal to prevent leakage of blood between the left atrium 16 and the left ventricle 20, for example, when the apparatus $10_a$ is implanted in a heart 12. The apparatus $10_a$ shown in FIGS. 6A-E can be used to replace a native mitral valve 30, for example, using any one or combination of known surgical methods. As shown in FIG. 7, for example, an apical puncture method can be used to deliver the apparatus $10_a$ shown in FIG. 6A to a native mitral valve 30. It will be appreciated, however, that other percutaneous, transvascular, and/or open surgical methods may be used to deliver the apparatus $10_a$ to a native mitral valve 30. It will also be appreciated that the method of the present invention will typically entail gaining access to a beating heart 12; however, the present invention may also be used for intravascular stopped-heart access as well as stopped-heart open chest procedures.

The apparatus $10_a$ shown in FIG. 6A can be delivered to a native mitral valve 30 using an apical puncture method similar or identical to the apical puncture method described above. Briefly, one step of the method can include placing the apparatus $10_a$ into a delivery catheter 70. Prior to placing the apparatus $10_a$ into the delivery catheter 70, the dimensions of the native mitral valve 30 and the native mitral annulus 36 can be determined. After selecting an apparatus $10_a$ whose dimensions correspond to the dimensions of the native mitral valve 30 and the native mitral annulus 36, a puncture tool 76 can be used to puncture the chest wall. The puncture tool 76 can then be extended through the apical portion of the left ventricle 20 into the left ventricular chamber. Next, the delivery catheter 70 can be urged through the puncture tool 76 as shown in FIG. 7 so that the delivery catheter is positioned at a distal end portion 82 of the puncture tool.

Both the puncture tool 76 and the delivery catheter 70 can then be progressively withdrawn from the left ventricle 20 so that the expandable support member 56 can expand into contact with the native mitral annulus 36, and the rod-shaped members 98 can transition from the collapsed configuration to the expanded configuration. As the delivery catheter 70 and the puncture tool 76 are completely removed from the left ventricle 20, the rod-shaped members 98 located at the first and second ends 88 and 90 of the elongated body members 86 can respectively contact the superior and inferior aspects 78 and 80 of the mitral annulus 36 and thereby secure the apparatus $10_a$ in the native mitral annulus (FIG.

Figure 9:
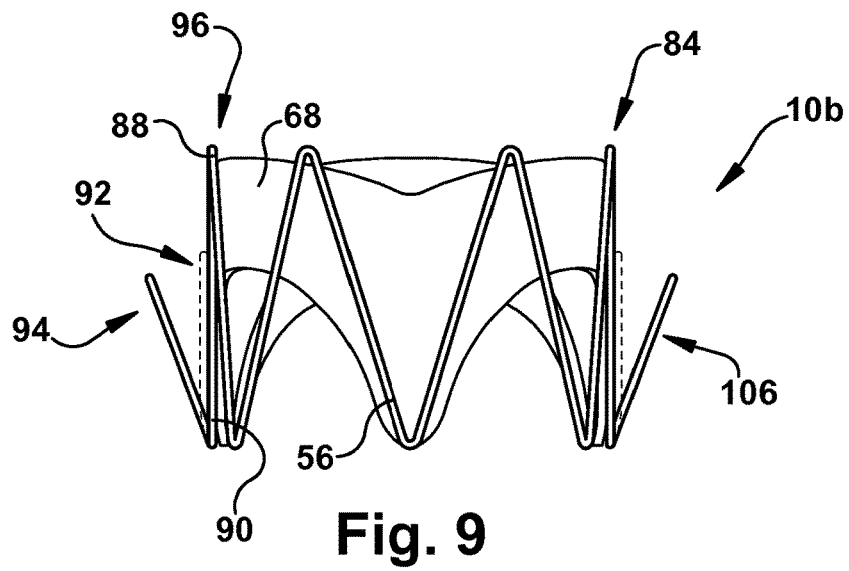
FIG. 9 is a cross-sectional view showing another alternative embodiment of the apparatus in FIG. 6A.
Figure 10:
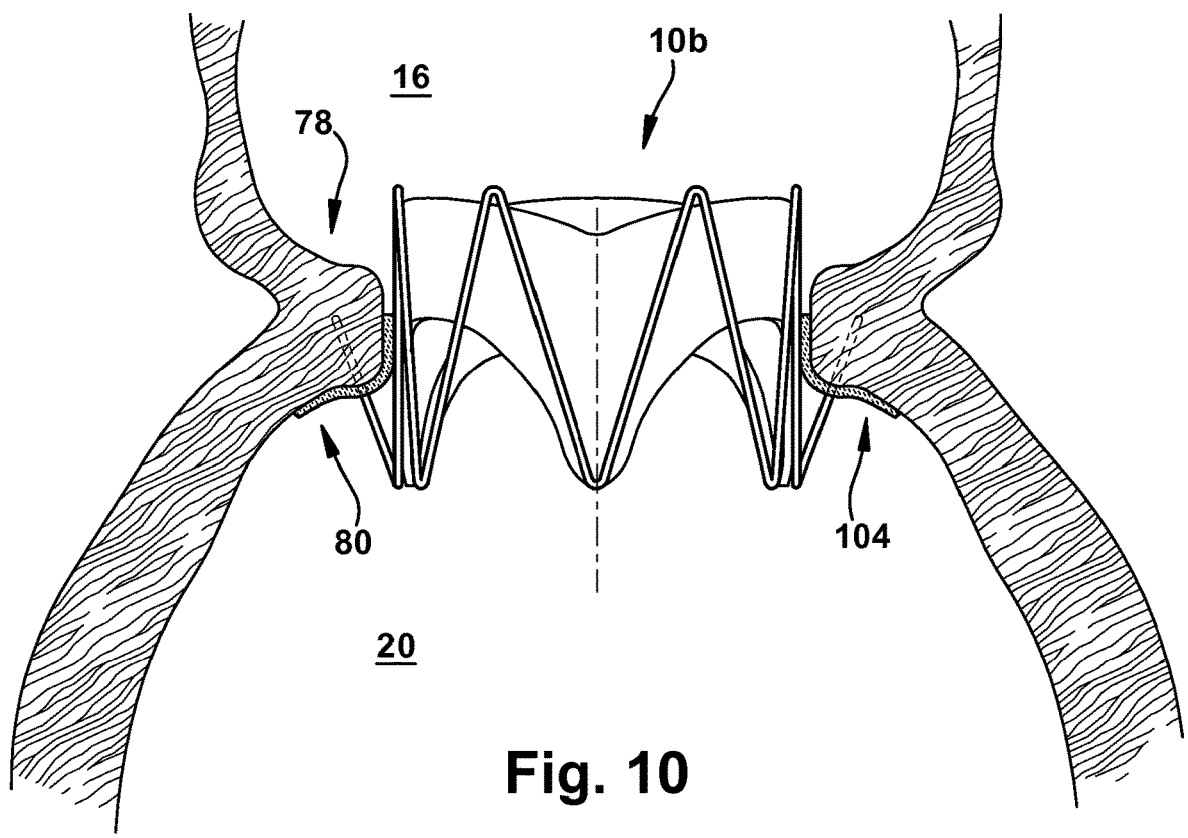

8). With the apparatus $10_a$ securely positioned in the native mitral annulus 36, normal blood flow can resume through the prosthetic valve 68. Another embodiment of the present invention is illustrated in FIG. 9.

The apparatus $10_b$ is identically constructed as the apparatus $10_a$ shown in FIGS. 6A-E, except where as described below. In FIG. 9, structures that are identical as structures in FIGS. 6A-E use the same reference numbers, whereas structures that are similar but not identical carry the suffix "b".

An apparatus $10_b$ for replacing a native cardiac valve, such as a mitral valve 30 can comprise an expandable support member 56 and a prosthetic valve 68 operably secured within the expandable support member. As shown in FIG. 9, the apparatus $10_b$ can further include a securing member 84 operably connected to the expandable support member 56. The securing member 84 can comprise an elongated body member 86 having a first end 88, a second end 90, and a main body portion 92 extending between the first and second ends. The securing member 84 can be operably secured to the expandable support member 56 using any one or combination of known fastening means (not shown), such as sutures, clips, pins, staples, adhesives, or the like.

The second end 90 of the elongated body member 86 can also include a first attachment member 94 operably connected thereto for embedding into the annular tissue at the inferior aspect of a native cardiac valve annulus. As shown in FIG. 9, the first attachment member 94 can include at least one rod-shaped puncturing member 106. The puncturing member 106 can have a fixed length or, alternatively, the puncturing member can have a compressible, spring-like configuration (not shown). The puncturing member 106 can have a needle- or barb-like shape to facilitate penetration of the puncturing member into annular tissue.

The apparatus $10_b$ is capable of transitioning between a collapsed configuration and an expanded configuration. As shown in FIG. 9, the puncturing member 106 can extend substantially axial to the elongated body member 86 in the expanded configuration. In the collapsed configuration (indicated by the dashed lines), the puncturing member 106 can extend substantially parallel to the elongated body member 86. As described in more detail below, the puncturing member 106 can be used to secure the apparatus $10_b$ in a native cardiac valve annulus.

The apparatus $10_b$ shown in FIG. 9 can be delivered to a native cardiac valve, such as a mitral valve 30 using an apical puncture method similar or identical to the apical puncture method described above. Briefly, one step of the method can include placing the apparatus $10_b$ into a delivery catheter 70. Prior to placing the apparatus $10_b$ into the delivery catheter 70, the dimensions of the native mitral valve 30 and the native mitral annulus 36 can be determined. After selecting an apparatus $10_b$ whose dimensions correspond to the dimensions of the native mitral valve 30 and the native mitral annulus 36, the puncture tool 76 can be used to puncture the chest wall. The puncture tool 76 can then be extended through the apical portion of the left ventricle 20 into the left ventricular chamber. Next, the delivery catheter 70 can be urged through the puncture tool 76 so that the delivery catheter is positioned at a distal end portion 82 of the puncture tool (not shown).

Both the puncture tool 76 and the delivery catheter 70 can then be progressively withdrawn from the left ventricle 20 so that the expandable support member 56 expands into contact with the native mitral annulus 36. As the delivery catheter 70 and the puncture tool 76 are completely removed from the left ventricle 20, each of the puncture members 106 can transition from the collapsed configuration to the expanded configuration. In the expanded configuration, each of the puncture members 106 can penetrate into the annular tissue at the inferior aspect 80 of the native mitral annulus 36 and thereby secure the apparatus $10_b$ in the native mitral annulus (FIG. 1C). With the apparatus $10_b$ securely positioned in the native mitral annulus 36, normal blood flow can resume through the prosthetic valve 68.

Figure 11:
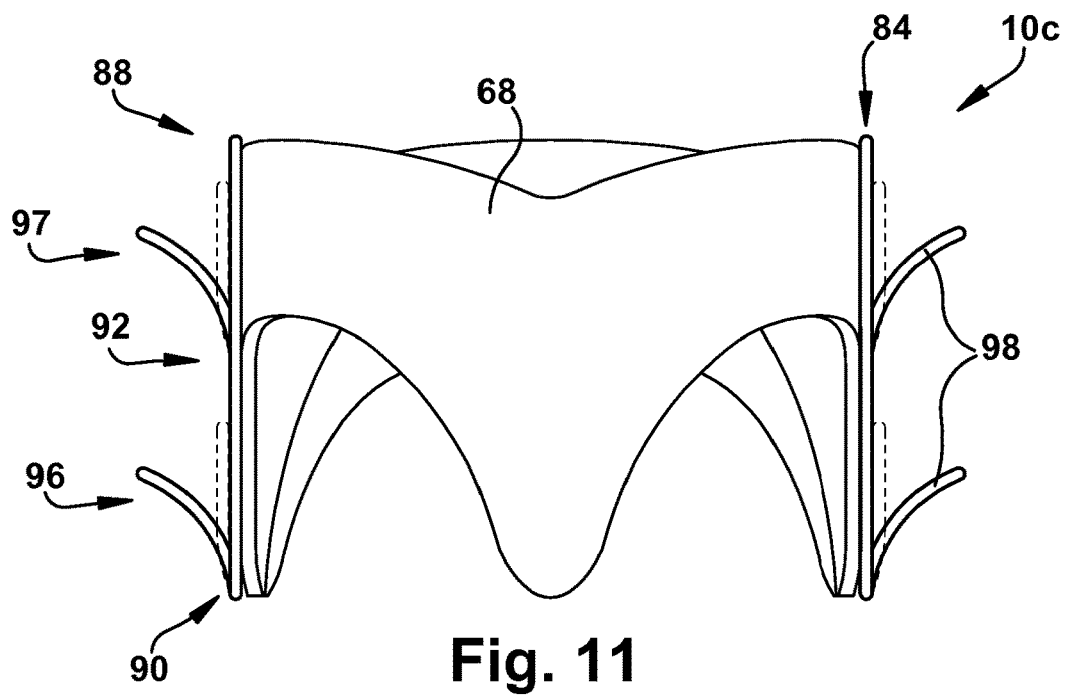
FIG. 11 is a cross-sectional view showing another alternative embodiment of the apparatus in FIG. 6A.

Another embodiment of the present invention is illustrated in FIG. 11. The apparatus $10_c$ is identically constructed as the apparatus $10_a$ shown in FIGS. 6A-E, except where as described below. In FIG. 11, structures that are identical as structures in FIGS. 6A-E use the same reference numbers, whereas structures that are similar but not identical carry the suffix "c".

An apparatus $10_c$ for replacing a native cardiac valve, such as a mitral valve 30 can comprise a prosthetic valve 68 operably secured to a securing member 84. The securing member 84 can comprise an elongated body member 86 having a first end 88, a second end 90, and a main body portion 92 extending between the first and second ends. The securing member 84 can be operably secured to the prosthetic valve 68 using any one or combination of known fastening means (not shown), such as sutures, clips, pins, staples, adhesives, or the like.

The second end 90 of the elongated body member 86 can include a first attachment member 94 operably connected thereto for contacting the inferior aspect of a native cardiac valve annulus when the apparatus $10_c$ is in an expanded configuration. As shown in FIG. 11, the first end 88 of the elongated body member 86 can also include a second attachment member 96 operably connected thereto for contacting the superior aspect of a native cardiac valve annulus when the apparatus $10_c$ is in an expanded configuration. The first and second attachment members 94 and 96 can be made from any one or combination of flexibly resilient, medical grade materials, including, for example, Nitinol, stainless steel, or other suitable metals or plastics having shape memory characteristics.

The first and second attachment members 94 and 96 can have a variety of configurations. As shown in FIG. 11, for example, the first and second attachment members 94 and 96 can include flexible, rod-shaped members 98. It will be appreciated, however, that the first and second attachment members 94 and 96 can also comprise any one or combination of the structures illustrated in FIGS. 6A-E. The rod-shaped members 98 can be joined to or integrally formed with the elongated body member 86 so that the rod-shaped members can transition from a collapsed configuration (indicated by dashed lines) to an expanded configuration. In the collapsed configuration, the rod-shaped members 98 can extend substantially parallel to the elongated body member 86. In the expanded configuration, the rod-shaped members 98 can extend substantially axial to the elongated body member 86. As described in more detail below, the rod-shaped members 98 located at the first and second ends 88 and 90 of the elongated body member 86 can respectively contact the superior and inferior aspects 78 and 80 of the mitral annulus 36 when the apparatus $10_c$ is in an expanded configuration.

The apparatus $10_c$ shown in FIG. 11 can be used to replace a native cardiac valve, such as a native mitral valve 30 using an apical puncture method similar or identical to the apical puncture method described above. Briefly, one step of the method can include placing the apparatus $10_c$ into a delivery catheter 70. Prior to placing the apparatus $10_c$ into the delivery catheter 70, the dimensions of the native mitral valve 30 and the native mitral annulus 36 can be determined. After selecting an apparatus 10$_c$ whose dimensions correspond to the dimensions of the native mitral valve 30 and the native mitral annulus 36, a puncture tool 76 can be used to puncture the chest wall. The puncture tool 76 can then be extended through the apical portion of the left ventricle 20 into the left ventricular chamber. Next, the delivery catheter 70 can be urged through the puncture tool 76 so that the delivery catheter is positioned at a distal end portion 82 of the puncture tool (not shown).

Figure 12:
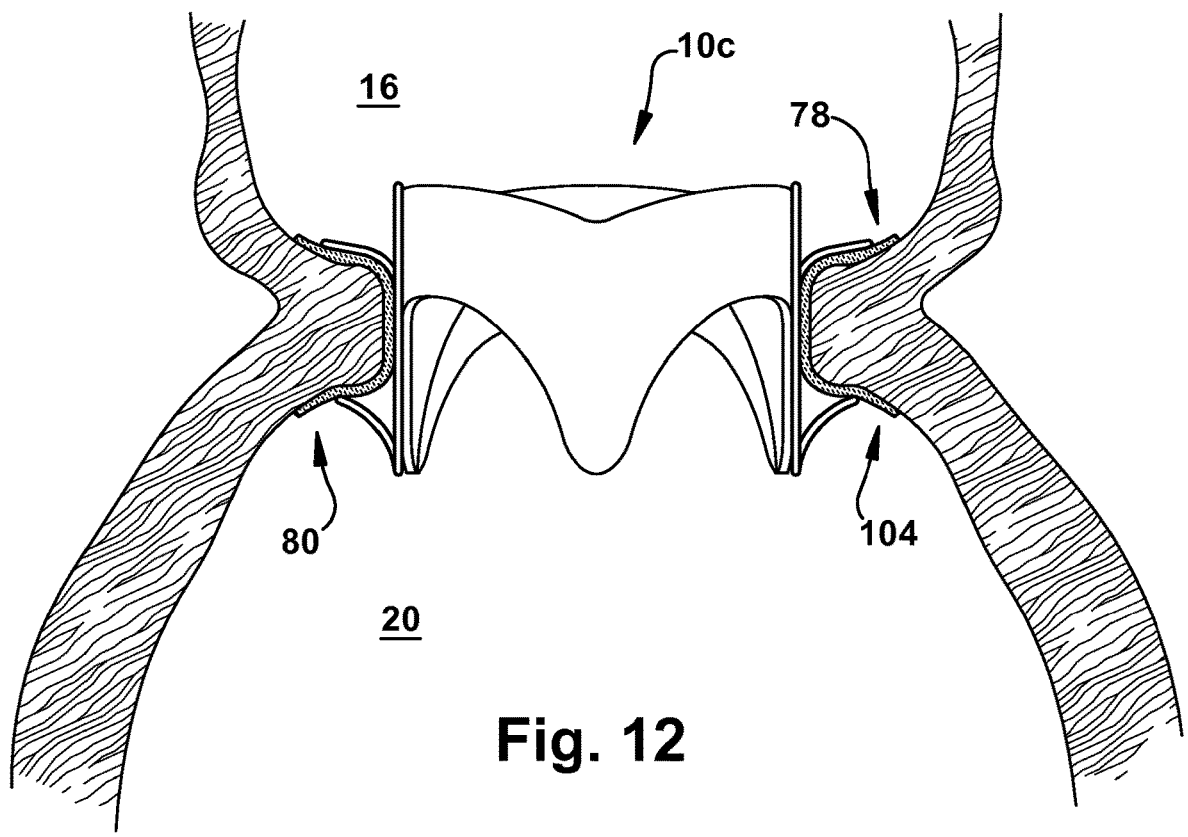
FIG. 12 is a cross-sectional view showing the apparatus of FIG. 11 implanted in a native mitral valve.

Both the puncture tool 76 and the delivery catheter 70 can then be progressively withdrawn from the left ventricle 20 so that prosthetic valve 68 expands into contact with the native mitral annulus 36, and the rod-shaped members 98 located at the first end 88 of each of the elongated body members 86 transitions from the collapsed configuration to the expanded configuration. As the delivery catheter 70 and the puncture tool 76 are completely removed from the left ventricle 20, the rod-shaped members 98 located at the first and second ends 88 and 90 of each of the elongated body members 86 can respectively contact the superior and inferior aspects 78 and 80 of the mitral annulus 36, thereby securing the apparatus 10$_c$ in the native mitral annulus (FIG. 12). With the apparatus 10$_c$ securely positioned in the native mitral annulus 36, normal blood flow can resume through the prosthetic valve 68.

From the above description of the invention, those skilled in the art will perceive improvements, changes and modifications. For example, it will be appreciated that the methods of the present invention can include implanting an expandable anchoring member 42 or an expandable support member 56, without a prosthetic valve 68 attached therein, in a native cardiac valve annulus. After the expandable anchoring member 42 or the expandable support member 56 is securely positioned in the native cardiac valve annulus, a prosthetic valve 68 can then be secured therein using any one or combination of known fastening means. Such improvements, changes and modifications are within the skill of the art and are intended to be covered by the appended claims.

Having described the invention, we claim:

1. An apparatus for replacing a native mitral valve or a native tricuspid valve, comprising:
    a radially expandable and compressible annular anchoring member comprising a mesh structure defining a plurality of circumferentially extending rows of cells that extend continuously around the anchoring member, wherein the anchoring member is configured to contact and anchor against tissue of the native mitral valve or the native tricuspid valve;
    a fabric layer attached to and covering an inner surface of the anchoring member, the fabric layer made of Dacron;
    a radially expandable and compressible annular support member disposed within the anchoring member, wherein the support member is pre-attached to the anchoring member with sutures before placing the apparatus in a delivery catheter; and
    a prosthetic valve disposed within and secured to the support member;
    wherein the apparatus is radially compressible to a radially compressed state for placing the apparatus in the delivery catheter and delivering the apparatus to the native mitral valve or the native tricuspid valve and wherein the apparatus can radially expand to a radially expanded state when released from the delivery catheter;
    wherein the anchoring member and the support member are made of Nitinol and wherein the apparatus can self-expand from the radially compressed state to the radially expanded state when released from the delivery catheter;
    wherein the fabric layer is disposed in between the anchoring member and the support member.

2. The apparatus of claim 1, wherein the fabric layer also extends over a portion of an outer surface of the anchoring member.

3. The apparatus of claim 1, wherein the anchoring member comprises an inlet end portion, an outlet end portion, and a main body portion extending between the inlet end portion and the outlet end portion, wherein when the apparatus is in the radially expanded state, the inlet end portion of the anchoring member extends radially outwardly from the main body portion and is configured to contact a superior aspect of the native mitral valve or the native tricuspid valve, and wherein when the apparatus is in the radially expanded state, the inlet end portion has a greater diameter than the main body portion.

4. The apparatus of claim 1, wherein the anchoring member is capable of conforming to a shape of an annulus of the native mitral valve or the native tricuspid valve when implanted therein.

5. The apparatus of claim 1, wherein the support member has an inlet end that is spaced downstream from an inlet end of the anchoring member.

6. The apparatus of claim 1, wherein the anchoring member is bioabsorbable.

7. The apparatus of claim 1, wherein the support member comprises a mesh-like configuration.

8. The apparatus of claim 1, wherein support member has a first length extending from an inlet end to an outlet end of the support member, the anchoring member has a second length extending from an inlet end to an outlet end of the anchoring member, wherein the second length is greater than the first length, and wherein an entirety of the support member is disposed within the anchoring member.

9. The apparatus of claim 1, wherein the support member is cylindrical.

10. An apparatus for replacing a native atrioventricular valve, comprising:
    a radially expandable and compressible annular anchoring member comprising a first end portion, a second end portion, and a main body portion extending between the first and second end portions, wherein the main body portion is configured to contact and conform to an annulus of the native atrioventricular valve when implanted therein, wherein the anchoring member comprises a mesh structure defining a plurality of circumferentially extending rows of cells that extend continuously around the anchoring member;
    a fabric layer attached to and covering an inner surface of the anchoring member;
    a radially expandable and compressible annular support member disposed within and pre- attached to the anchoring member before placing the apparatus in a delivery catheter; and
    a prosthetic valve disposed within and secured to the support member;
    wherein the apparatus is radially compressible to a radially compressed state for placing the apparatus in the delivery catheter and delivering the apparatus to the native atrioventricular valve and wherein the apparatus can radially expand to a radially expanded state when released from the delivery catheter;

wherein the anchoring member and the support member are made of Nitinol and wherein the apparatus can self-expand from the radially compressed state to the radially expanded state when released from the delivery catheter;

wherein the fabric layer is disposed in between the anchoring member and the support member.

11. The apparatus of claim 10, wherein the main body portion of the anchoring member has an inner surface defining a channel and wherein the support member and the prosthetic valve are disposed within the channel.

12. The apparatus of claim 10, wherein the fabric layer is attached to an outer surface of the anchoring member.

13. The apparatus of claim 10, wherein when the apparatus is in the radially expanded state, the first end portion of the anchoring member extends radially outwardly from the main body portion and is configured to contact a superior aspect of the native atrioventricular valve.

14. The apparatus of claim 10, wherein the prosthetic valve has an inlet end and an outlet end, wherein the inlet end of the prosthetic valve is spaced downstream from an inlet end of the anchoring member and the outlet end of the prosthetic valve is spaced upstream from an outlet end of the anchoring member.

15. The apparatus of claim 10, wherein the anchoring member includes radiopaque markers.

16. The apparatus of claim 10, wherein the prosthetic valve comprises a dry tissue valve.

17. The apparatus of claim 10, wherein the prosthetic valve comprises biological tissue that has been cross-linked using glutaraldehyde.

18. An apparatus for replacing a native atrioventricular valve, comprising:

a radially expandable and compressible annular anchoring member comprising an inlet end portion, an outlet end portion, and a main body portion extending between the inlet end portion and the outlet end portion, the main body portion configured to contact and conform to the annulus of the native atrioventricular valve when implanted therein, wherein the anchoring member comprises a mesh structure defining a plurality of circumferentially extending rows of cells that extend continuously around the anchoring member;

a fabric layer attached to and covering an inner surface of the anchoring member;

a radially expandable and compressible annular support member disposed within and fixed to the anchoring member; and a prosthetic valve disposed within and secured to the support member;

wherein the apparatus is radially compressible to a radially compressed state in which the support member is disposed in and pre-attached to the anchoring member, wherein when the apparatus is in the radially compressed state with the support member disposed in and pre- attached to the anchoring member, the apparatus can be placed in a delivery catheter and delivered to the native atrioventricular valve, and wherein the apparatus can radially expand to a radially expanded state when released from the delivery catheter;

wherein the anchoring member and the support member are made of Nitinol and wherein the apparatus can self-expand from the radially compressed state to the radially expanded state when released from the delivery catheter;

wherein the fabric layer is disposed in between the anchoring member and the support member.

19. The apparatus of claim 18, wherein when the apparatus is in the radially expanded state, the inlet end portion of the anchoring member extends radially outwardly from the main body portion and is configured to contact a superior aspect of the native atrioventricular valve.

* * * * *